US010034802B2

(12) United States Patent
Macura et al.

(10) Patent No.: US 10,034,802 B2
(45) Date of Patent: *Jul. 31, 2018

(54) FORCED FOCUSED FASTENING MEMBER

(71) Applicant: The Procter & Gamble Company, Cincinnati, OH (US)

(72) Inventors: Anna Elizabeth Macura, Loveland, OH (US); Mark James Kline, Okeana, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 433 days.

This patent is subject to a terminal disclaimer.

(21) Appl. No.: 14/883,669

(22) Filed: Oct. 15, 2015

(65) Prior Publication Data

US 2016/0030259 A1 Feb. 4, 2016

Related U.S. Application Data

(63) Continuation of application No. 14/179,823, filed on Feb. 13, 2014, now Pat. No. 9,211,221, which is a (Continued)

(51) Int. Cl.
*A61F 13/15* (2006.01)
*A61F 13/20* (2006.01)
(Continued)

(52) U.S. Cl.
CPC .......... *A61F 13/5633* (2013.01); *A61F 13/58* (2013.01); *A61F 13/62* (2013.01);
(Continued)

(58) Field of Classification Search
CPC ...... A61F 13/5633; A61F 13/58; A61F 13/62; A61F 13/622
See application file for complete search history.

(56) References Cited

U.S. PATENT DOCUMENTS 4,856,504 A 8/1989 Yamamoto et al.
4,861,652 A 8/1989 Lippert et al.
(Continued)

FOREIGN PATENT DOCUMENTS

EP 433951 A2 12/1990
EP 433951 B1 8/1996
(Continued)

OTHER PUBLICATIONS

PCT International Search Report, PCT/IB2006/054902, dated May 14, 2007 (11 pages).

*Primary Examiner* — Michele M Kidwell
(74) *Attorney, Agent, or Firm* — Wednesday G. Shipp; Andrew J. Hagerty

(57) ABSTRACT

A force focused fastening system maintaining a fastener element in plane during fastening. The force focused fastening system includes a force focused fastening member including an extensible region and an end region. The end region includes a fastener element and the extensible region includes a high modulus region aligned relative to a center portion of the fastener element. During fastening, the force focused fastening member directs forces toward the center portion of the fastener element, away from end portions, minimizing distortion of the fastener element.

20 Claims, 19 Drawing Sheets

Related U.S. Application Data continuation of application No. 13/368,740, filed on Feb. 8, 2012, now Pat. No. 8,690,852, which is a continuation of application No. 11/303,687, filed on Dec. 16, 2005, now Pat. No. 8,118,801.

(51) Int. Cl.
    *A61F 13/56* (2006.01)
    *A61F 13/58* (2006.01)
    *A61F 13/62* (2006.01)

(52) U.S. Cl.
    CPC .............. *A61F 13/622* (2013.01); *Y10T 24/27* (2015.01); *Y10T 24/2758* (2015.01); *Y10T 24/32* (2015.01); *Y10T 24/33* (2015.01); *Y10T 24/45225* (2015.01)

(56) References Cited

U.S. PATENT DOCUMENTS

| | | |
|---|---|---|
| 4,916,005 A | 4/1990 | Lippert et al. |
| 5,234,423 A | 8/1993 | Alemany et al. |
| 5,399,219 A | 3/1995 | Roessler et al. |
| 5,527,302 A | 6/1996 | Endres et al. |
| 5,580,411 A | 12/1996 | Nease et al. |
| 5,683,533 A | 11/1997 | Keighley et al. |
| 5,705,013 A | 1/1998 | Nease et al. |
| 5,797,824 A | 8/1998 | Tracy |
| 5,947,946 A | 9/1999 | Fisher et al. |
| 6,117,121 A | 9/2000 | Faulks et al. |
| 6,132,411 A | 10/2000 | Huber et al. |
| 6,692,477 B2 | 2/2004 | Gibbs |
| 6,994,698 B2 | 2/2006 | Leak et al. |
| 7,056,411 B2 | 6/2006 | Desai et al. |
| 7,432,413 B2 | 10/2008 | Roe et al. |
| 7,534,481 B2 * | 5/2009 | Seth ..................... B32B 25/00 428/172 |
| 7,799,162 B2 | 9/2010 | Wood et al. |
| 8,118,801 B2 | 2/2012 | Macura et al. |
| 8,690,852 B2 | 4/2014 | Macura et al. |
| 9,211,221 B2 * | 12/2015 | Macura ................. A61F 13/58 |
| 2003/0100878 A1 | 5/2003 | Leak et al. |
| 2003/0109844 A1 | 6/2003 | Gibbs |
| 2005/0215972 A1 | 9/2005 | Roe et al. |
| 2005/0215973 A1 | 9/2005 | Roe et al. |
| 2007/0142798 A1 | 6/2007 | Goodlander et al. |
| 2007/0142806 A1 | 6/2007 | Roe et al. |
| 2012/0143165 A1 | 6/2012 | Macura et al. |
| 2014/0163512 A1 | 6/2014 | Macura et al. |

FOREIGN PATENT DOCUMENTS

| | | |
|---|---|---|
| WO | WO-2001/087213 A1 | 11/2001 |
| WO | WO-2001/087588 A2 | 11/2001 |
| WO | WO-2002/013747 A1 | 2/2002 |

* cited by examiner

Example Grid Worksheet

Example Grid Worksheet

FORCED FOCUSED FASTENING MEMBER

FIELD OF THE INVENTION

This invention is directed to hygienic absorbent articles, such as diapers, pant style diapers, training pants and the like. Particularly, the invention is directed to a force focused fastening member used in such hygienic absorbent articles.

BACKGROUND OF THE INVENTION

Infants and other incontinent individuals wear absorbent articles such as diapers to receive and contain urine and other body exudates. Absorbent articles function both to contain the discharged materials and to isolate these materials from the body of the wearer and from the wearer's garments and bed clothing. In typical diaper-like absorbent articles, the article is affixed to a wearer by wrapping front and back halves of the article about a wearer's waist and hips and attaching one or more fasteners that hold front and back halves together. Although many fasteners are known, fasteners for absorbent articles such as diapers are typically surface fasteners.

Surface fasteners, such as hook & loop type fasteners (Velcro), adhesive fasteners, and cohesive fasteners, are common in the art. These fasteners require aligning an engaging surface to a receiving surface in a face-to-face relationship and then making contact to form a reliable connection. In order for contact to be made, the engaging and receiving surfaces need to be reasonably flat or at least have generally the same shape at the time of engagement. Forces often act on such surface fasteners during engagement affecting the shape of the engaging and receiving surfaces. Such forces have a tendency to cause the engaging and receiving surfaces to buckle out of plane, commonly referred to as curling. Curling may result in at least a portion of the first surface not making good contact with the second surface at engagement, potentially compromising fastening performance in use.

Fasteners are typically attached to the diaper via some intermediate material such as a nonwoven, film, or stretch laminate forming a panel. A fastener element is typically attached inboard of the edges of the panel to provide a gripping region to facilitate fastening. Gripping regions are generally stabilized by the user's grip, but regions outboard the gripped area are subject to forces that act to bend and/or buckle the fastener element. For example, referring to a prior art fastening member depicted in FIG. 1, a user grips a fastener over length, Lg, and pulls in a lateral direction. Lateral tension, $T_c$, builds in the system and distributes from the gripped region through the longitudinal fastener length, $L_f$. Tensions along the longitudinal end edges, $T_e$, act to bend end edges of fasteners out of plane. Tensions in the longitudinal direction, P, generated from Poisson effects (necking), act to buckle fasteners lengthwise. Shorter lengths are harder to buckle than longer lengths.

Therefore, a need exists for a fastener system capable of reducing curling during fastening. The present invention provides a fastening system that directs the majority of the forces toward the longitudinal center of a fastener element and away from the ends thereof in order to minimize distortion during fastening.

SUMMARY OF THE INVENTION

The present invention provides a force focused fastening system for a disposable absorbent article. The fastening system comprises a force focused fastening member having a longitudinal axis and a transverse axis. The force focused fastening member includes an extensible region and an end region. The extensible region has a proximal edge, a distal edge transversely opposite the proximal edge and two connecting edges joining the proximal edge to the distal edge. The end region extends transversely from the distal edge. A fastener element is disposed on the force focused fastening member at the end region. The fastener element has a longitudinal length, $L_f$, a transverse width, $W_f$, a center portion aligned relative to the transverse axis and two end portions longitudinally spaced from the center portion. The extensible region of the force focused fastening member has a modulus wherein the modulus in a least a portion of the extensible region adjacent the end region varies longitudinally and comprises at least one high modulus region having a longitudinal length, $L_h$, and a transverse width, $W_h$. The extensibility of the high modulus region is at least 10% lower than the extensibility of any other area in the extensible region. The high modulus region is aligned relative to the center portion of the fastener element such that the length of the offset between the longitudinal centerline of the high modulus region and the longitudinal centerline of the fastener element is less than 75% $L_f$. In addition, the high modulus region is spaced apart from the two end portions of the fastener element such that it is offset from the two end portions of the fastener element by lengths which are less than or equal to 40% $L_f$. As a result, a fastening system is provided where fastening forces are focused on the center portion of the fastener element, away from the two end portions.

BRIEF DESCRIPTION OF THE DRAWINGS

While this specification concludes with claims particularly pointing out and distinctly claiming that which is regarded as forming the present invention, it is anticipated that the invention can be more readily understood through reading the following detailed description of the invention and study of the accompanying drawings.

DETAILED DESCRIPTION OF THE INVENTION

Definitions

Figure 1:
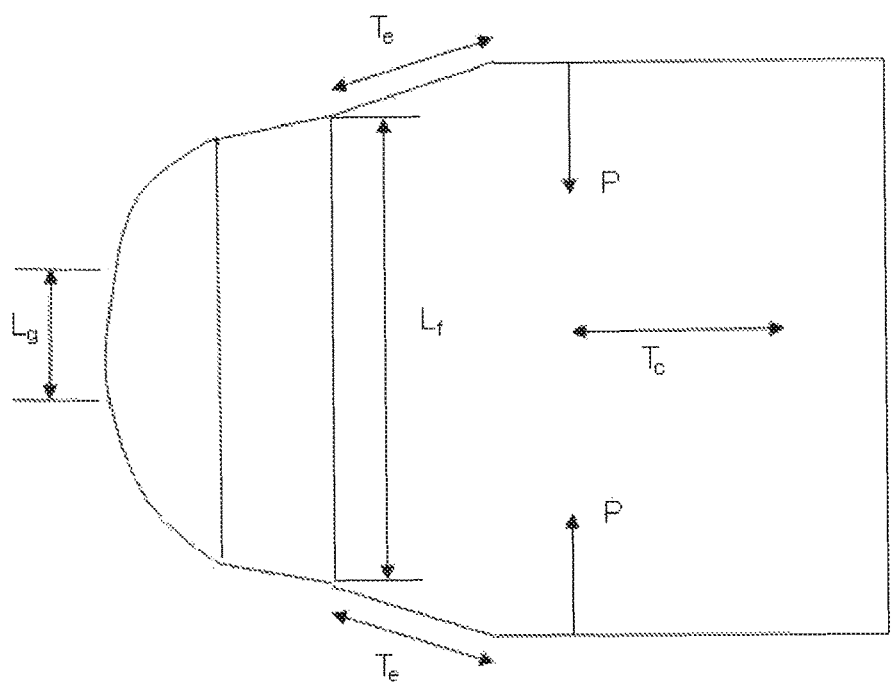
FIG. 1 is a plan view of a prior art fastening member illustrating how buckling forces are produced at the fastening element.

As used herein, the following terms have the following meanings:

"Absorbent article" refers to devices that absorb and contain liquid, and more specifically, refers to devices that are placed against or in proximity to the body of the wearer to absorb and contain the various exudates discharged from the body.

"Longitudinal" unless otherwise provided hereunder, refers to a direction running parallel to the maximum linear dimension of the article and includes directions within ±45° of the longitudinal direction.

The "lateral" or "transverse" direction is orthogonal to the longitudinal direction.

The "Z-direction" is orthogonal to both the longitudinal and transverse directions.

The "x-y plane" refers to the plane congruent with the longitudinal and transverse directions.

As used herein, the term "disposed" is used to mean that an element(s) is formed (joined and positioned) in a particular place or position as a unitary structure with other elements or as a separate element joined to another element.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

A "unitary" absorbent article refers to absorbent articles which are formed of separate parts united together to form a coordinated entity so that they do not require separate manipulative parts like a separate holder and liner.

The terms "permeable" and "impermeable" refer to the penetrability of materials in the context of the intended usage of disposable absorbent articles. Specifically, the term "permeable" refers to a layer or a layered structure having pores or openings that permit liquid water to pass through its thickness in the absence of a forcing pressure. Conversely, the term "impermeable" generally refers to articles and/or elements that are not penetrative by fluid through the entire Z-directional thickness of the article under pressure of 0.14 $lb/in^2$ or less. Preferably, the impermeable article or element is not penetrative by fluid under pressures of 0.5 $lb/in^2$ or less. More preferably, the impermeable article or element is not penetrative by fluid under pressures of 1.0 $lb/in^2$ or less.

The term "attached" refers to elements being connected or united by fastening, adhering, bonding, etc. by any method suitable for the elements being fastened, secured, or joined, together and their constituent materials. Many suitable methods for attaching elements together are well-known, including adhesive bonding, pressure bonding, thermal bonding, mechanical fastening, etc. Such attachment methods may be used to attach elements together over a particular area either continuously or intermittently. The term "attached" includes elements which are integrally formed with another element.

The terms "corrugations" or "rugosities" are used to describe hills and valleys that occur in a substrate or in a laminated structure. Neither term, i.e. "corrugations" nor "rugosities", mandates that either the hills or valleys created are uniform in nature.

As used herein, the term "diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

The term "disposable" is used herein to describe absorbent articles that generally are not intended to be laundered or otherwise restored or reused as absorbent articles (i.e., they are intended to be discarded after a single use and, preferably, to be recycled, composted or otherwise discarded in an environmentally compatible manner).

As used herein "elastically extensible" refers to characteristics of extensible materials that have the ability to return to approximately their original dimensions after a force that extended the extensible material is removed. Herein, any material or element described as "extensible" may also be "elastically extensible" unless otherwise provided.

As used herein the term "stretch" means to forcibly extend in length or width.

"Live stretch" includes stretching elastic and bonding the stretched elastic to a nonwoven. After bonding the stretched elastic is released causing it to contract, resulting in a "corrugated" nonwoven. The corrugated nonwoven can stretch as the corrugated portion is pulled to about the point that the nonwoven reaches at least one original flat dimension. The elastic is preferably stretched at least 25% and more preferably at least 100% of its relaxed length when it is bonded to the nonwoven.

The terms "modulus" (moduli pl.) refers modulus of elasticity which is the ratio of an increment of a form of stress to an increment of a form of strain.

The terms "pant", "pant style diaper", "training pant", "closed diaper", "pre-fastened diaper", and "pull-on diaper", as used herein, refer to disposable garments having a waist opening and leg openings designed for infant or adult wearers. A pant can be configured such that the pant has a closed waist and leg openings prior to being donned on the wearer or the pant can be configured such that the waist is closed and the leg openings are formed while on the wearer. A pant may be preformed by any suitable technique including, but not limited to, attaching together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened, rear waist fastened). Examples of suitable pants are disclosed in U.S. Pat. No. 5,246,433; U.S. Pat. No. 5,569,234; U.S. Pat. No. 6,120,487; U.S. Pat. No. 6,120,489; U.S. Pat. No. 4,940,464; U.S. Pat. No. 5,092,861; U.S. Pat. No. 5,897,545; U.S. Pat. No. 5,957,908; and U.S. Patent Publication No. 2003/0233082 A1.

Figure 2A:
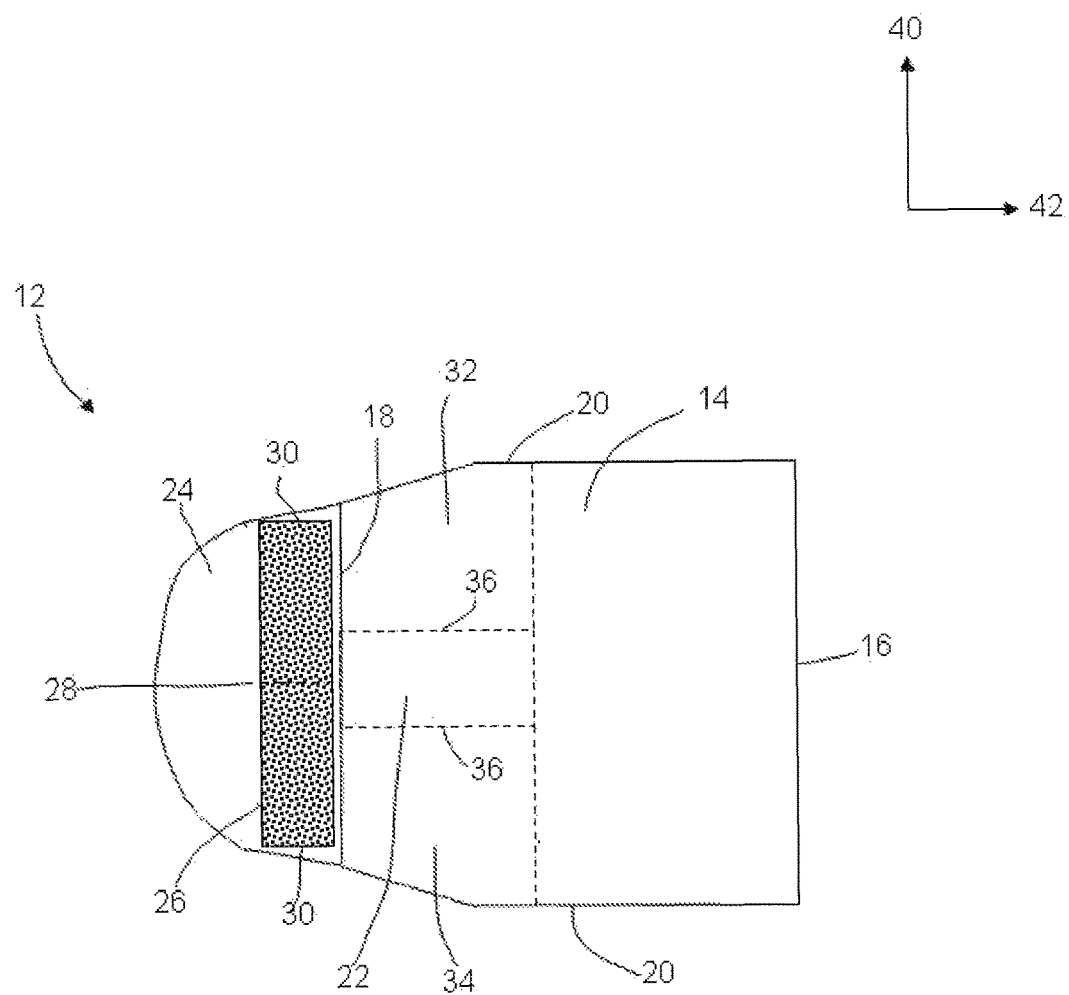
FIG. 2a is a plan view of force focused fastening member of the present invention.
Figure 2B:
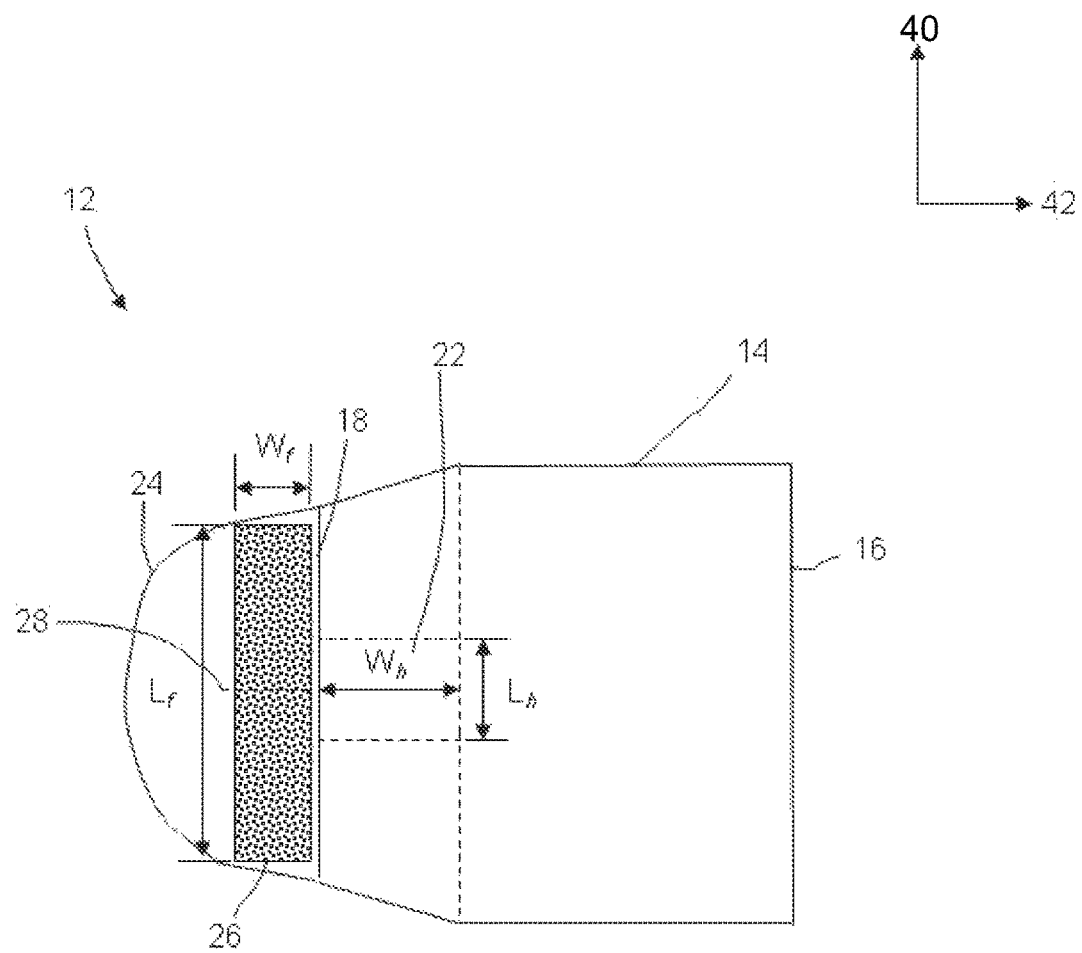
FIG. 2b is a plan view of the force focused fastening member of the present invention identifying dimensional parameters referred to throughout the specification.

Description:

Force focused fastening system 10 shown in FIGS. 2a and 2b is described in terms of a longitudinal direction 40 and a transverse direction 42. The longitudinal direction 40 is perpendicular to the direction of tension placed on the force focused fastening system 10. The transverse direction 42 is perpendicular to the longitudinal direction 40 and is parallel to the tension placed on the force focused fastening system 10. The force focused fastening system 10 comprises a force focused fastening member 12 having an extensible region 14 and an end region 24 disposed transversely from the extensible region 14. The extensible region has a proximal edge 16, a distal edge 18 transversely opposite the proximal edge 16 and a pair of connecting edges 20 joining the proximal edge 16 to the distal edge 18.

The end region 24 may be extensible but is preferably nonextensible. The end region 24 extends transversely from the distal edge 18 and includes a fastener element 26. The fastener element 26 has a center portion 28 and two end portions 30 longitudinally spaced from the center portions 28. The fastener element 26 can comprise any fastener for joining two surfaces but preferably includes surface fasteners such as hook and loop (Velcro), adhesives, cohesives, and even magnets.

The extensible region 14 of the force focused fastening member 12 has a modulus wherein the modulus in a least a portion of the extensible region 14 adjacent the end region 24 varies longitudinally and comprises at least one high modulus region 22. The high modulus region 22 is aligned relative to the center portion 28 of the fastener element 26 away from the two end portions 30. The extensibility of the high modulus region 22 may be at least 10% lower than the extensibility of any other area in the extensible region 14. The extensibility of the high modulus region 22 may be at least 25% lower or at least 50% lower than the extensibility of any other area in the extensible region 14. Alternatively, the extensibility of the high modulus region 22 may be at least 10% lower, at least 25% lower or at least 50% lower than the extensibility of at least one other area in the extensible region 14.

Borders 36 of the high modulus region 22 extend transversely along the extensible region 14. The borders 36 are spaced apart from the two end portions 30 of the fastener element 26 providing a first region 32 and a second region 34 adjacent the end portions 30 of the fastener element 26. The extensibility of the first region 32 and the second region 34 can be greater than or equal to 90% the extensibility of the high modulus region 22. Alternatively, the extensibility of the first and second regions 32, 34 can be greater than or equal to 75% or greater than or equal to 50% of the extensibility of the high modulus region 22. In addition, the extensibility of the first region 32 can be lower than, equal to, or greater than the extensibility of the second region 34.

As shown in FIG. 2b, the high modulus region 22 has a longitudinal length, $L_h$, and a transverse width, $W_h$. The fastener element 26 has a longitudinal length, $L_f$, and a transverse width, $W_f$. The longitudinal length, $L_h$, of the high modulus region 22 can be less than or equal to 80% the length, $L_f$, of the fastener element 26. Alternatively, the longitudinal length, $L_h$, of the high modulus region 22 can be less than or equal to 50% $L_f$ or less than or equal to 25% $L_f$.

The width, $W_h$, of the high modulus region 22 relative to the width, $W_f$, of the fastener element 26 also contributes to reduction in curl. The width, $W_h$, of the high modulus region 22 can be equal to or greater than 25% $W_f$. Alternatively, the width, $W_h$, of the high modulus region 22 can be equal to or greater than 100% $W_f$, equal to or greater than 200% $W_f$ or else cover the full width of the extensible region 14. For embodiments (described below) where the width, $W_h$, of the high modulus region 22 covers the full width of the force focused fastening member 12 from the proximal edge 16 to distal edge 18, the width, $W_h$, of the high modulus region 22 may extend transversely and longitudinally, the full width of the extensible region 14 providing tension bands directed to regions of an article associated with the force focused fastening system 10.

Figure 3:
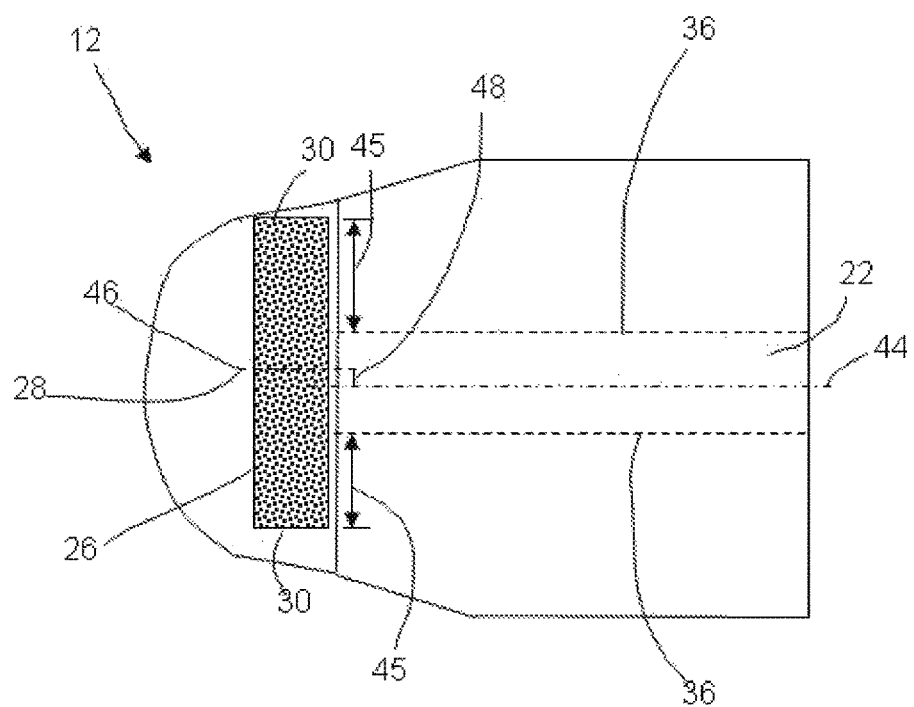
FIG. 3 is a plan view of the force focused fastening member of the present invention illustrating the offset between the longitudinal centerline of the fastener element and the longitudinal centerline of the high modulus region.

As previously explained, in effort to reduce curling of the fastening element 26 during fastening, fastening forces are focused toward the center portion 28 of the fastener element 26 and away from the end portions 30 of the fastener element 26. As shown in FIG. 3, this can be accomplished by aligning a longitudinal centerline 46 of the fastener element 26 with a longitudinal centerline 44 of the high modulus region 22. The longitudinal centerline 44 of the high modulus region 22 is aligned relative to the longitudinal centerline 46 of the fastener element 26 such that the length of an offset 48 between the two is minimal. The length of the offset 48 between a longitudinal centerline 44 of the high modulus region 22 and the longitudinal centerline 46 of the fastener element 26 can be less than 75% the length of the fastener element, $L_f$. Alternatively, the length of the offset 48 can be less than 25% $L_f$ or less than 10% $L_f$.

In addition, borders 36 of the high modulus region 22 are separated from the end portions 30 of the fastener element 26 by lengths 45. The lengths 45 separating the end portions 30 from the borders 36 can be the same or different. The lengths 45 can be greater than or equal to 25% $L_f$. Alternatively, the high modulus region 22 can be spaced apart from the two end portions 30 of the fastener element 26 such that the borders 36 of the high modulus region 22 are separated from the end portions 30 by lengths 45 greater than or equal 30% $L_f$. Preferably the borders 36 of the high modulus region 22 are separated from the end portions 30 by lengths greater than or equal to 40% $L_f$.

Figure 4A:
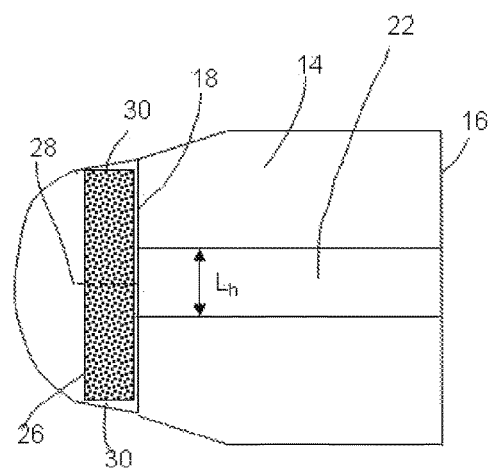
FIG. 4a is a plan view of the force focused fastening member of the present invention illustrating a high modulus region having a constant longitudinal height.
Figure 4B:
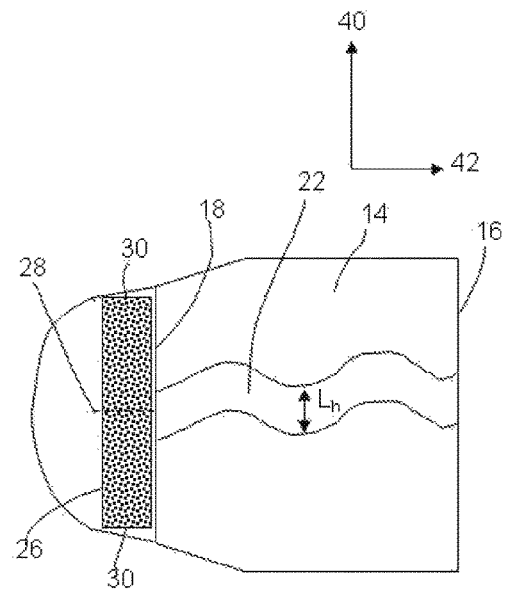
FIG. 4b is a plan view of the force focused fastening member of the present invention illustrating a high modulus region of constant height having a curvilinear pattern.

As illustrated in FIG. 4a-4d, the high modulus region 22 can be configured a number of different ways focusing the fastening forces on the center portion 28 of the fastener element 26 and away from the end portions 30. The embodiments shown in FIGS. 4a and 4b illustrate high modulus regions 22 of constant longitudinal length, $L_h$, extending from the distal edge 18 of the extensible region 14 to the proximal edge 16 of the extensible region 14. The high modulus region 22 in FIG. 4a has a linear configuration where as the high modulus region 22 in FIG. 4b has a curvilinear configuration.

Figure 4C:
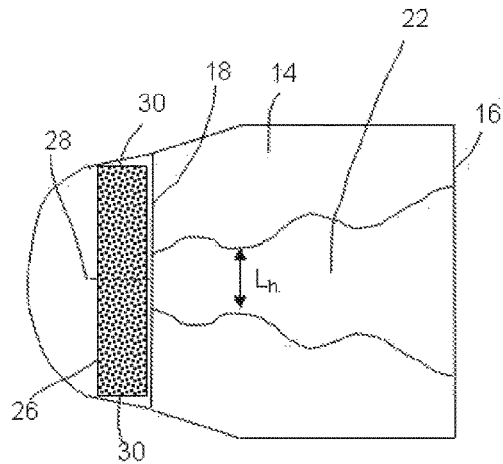
FIG. 4c is a plan view of the force focused fastening member of the present invention illustrating a high modulus region that varies in height transversely.
Figure 4D:
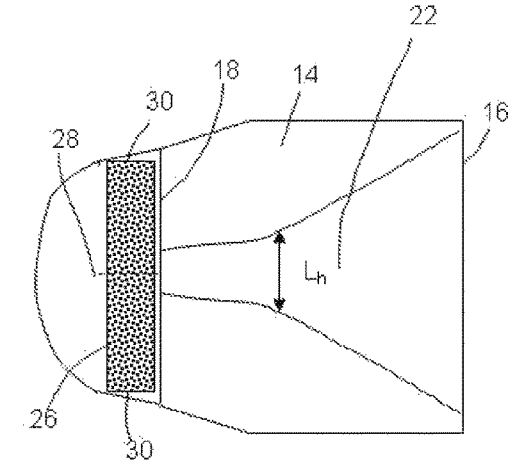
FIG. 4d is a plan view of the force focused fastening member of the present invention having a high modulus region that increases linearly from the fastener element.

Alternatively, the high modulus regions 22 for the embodiments shown in FIGS. 4c and 4d extend from the distal edge 18 of the high modulus region 22 to the proximal edge 16 of the high modulus region 22. For these embodiments, the longitudinal length, $L_h$, changes from the distal edge 18 to the proximal edge 16. In FIG. 4c, the longitudinal length, $L_h$, varies, gradually increasing from the distal edge 18 to the proximal edge 16. In FIG. 4d the longitudinal length continuously increases from the distal edge 18 to the proximal edge 16. In addition to the variations in the longitudinal length, $L_h$, of the high modulus region, the modulus of the high modulus region 22 can also vary transversely from the distal edge 18 to the proximal edge 16.

Figure 5A:
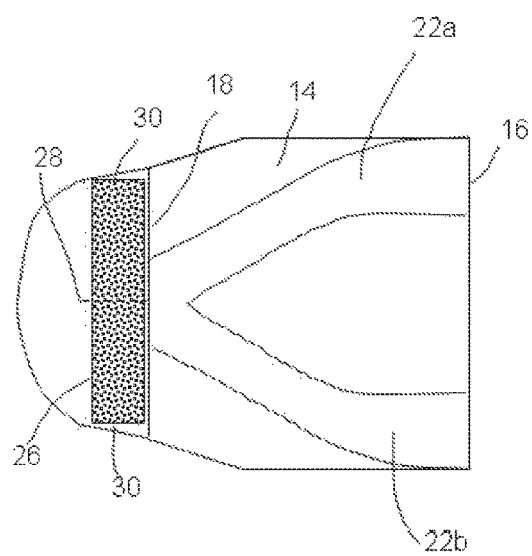
FIGS. 5a-5c are plan views of force focused fastening members of the present invention illustrating two or more high modulus regions extending transversely, converging on the center portion of the fastener element and diverging away from the fastener element.
Figure 5B:
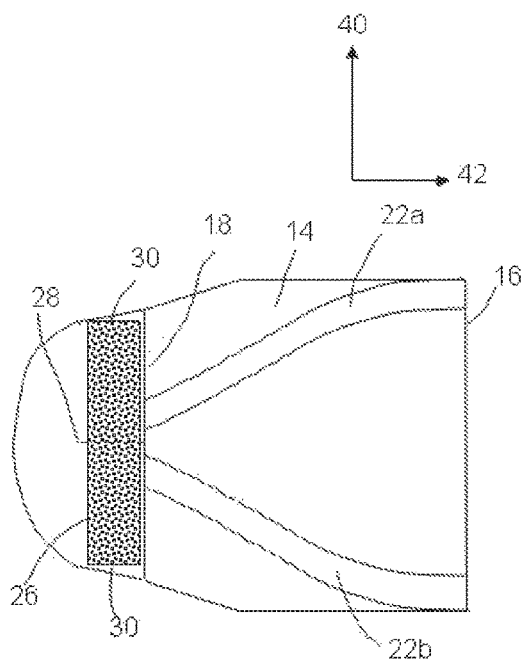
Figure 5C:
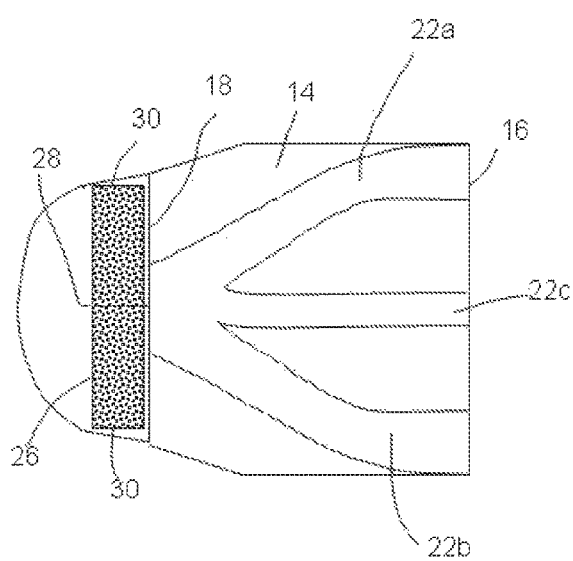

The high modulus region 22 can also be configured to direct tensions toward regions of an article such as the leg or waist regions of a diaper described in detail below. As shown in FIGS. 5a to 5c, the extensible region 14 can comprise two high modulus regions, 22a and 22b, aligned relative to the center portion 28 of the fastener element 26. FIGS. 5a and 5b illustrate configurations comprising a first high modulus region 22a and a second high modulus region 22b extending from the distal edge 18 to the proximal edge 16 of the extensible region 14. Each high modulus region 22a, 22b has an end converging on the center portion 28 of the fastener element 26 proximate the distal edge 18 of the extensible region 14 and an opposite end diverging toward a connecting edge 20 of the extensible region 14. FIG. 5c illustrates configuration including a third high modulus region 22c disposed between the first and second high modulus regions 22a, 22b. For embodiments including multiple high modulus regions, the modulus of each of the high modulus regions can be the same or different.

Figure 6A:
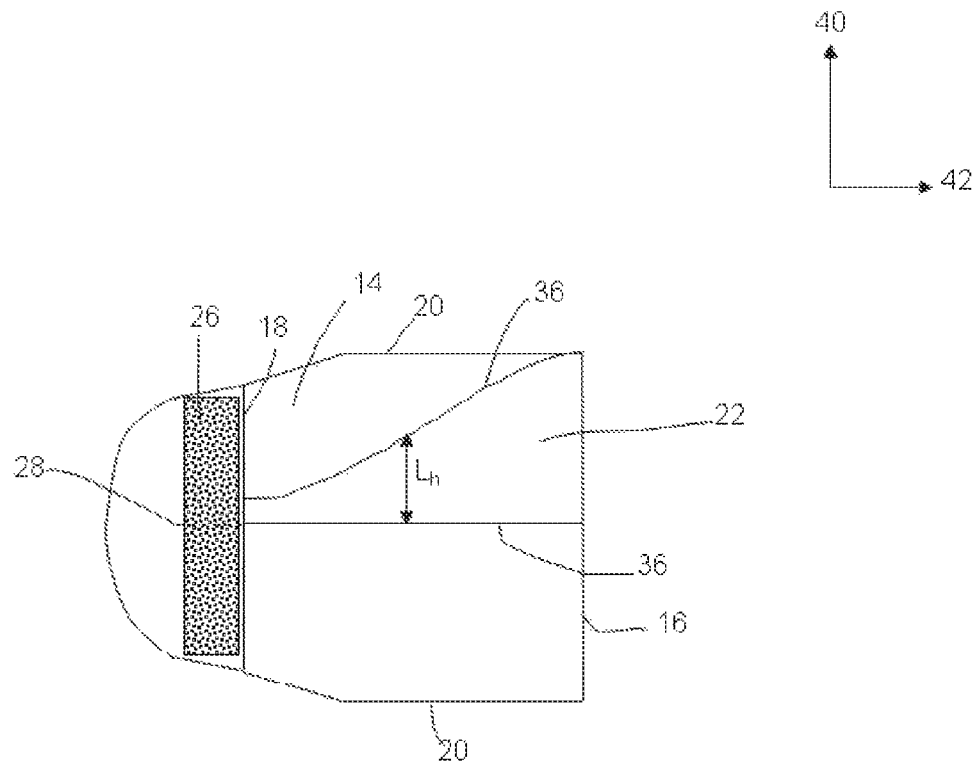
FIGS. 6a and 6b are plan views of the force focused fastening member of the present invention illustrating the high modulus region increasing in length transversely away from the fastener element.
Figure 6B:
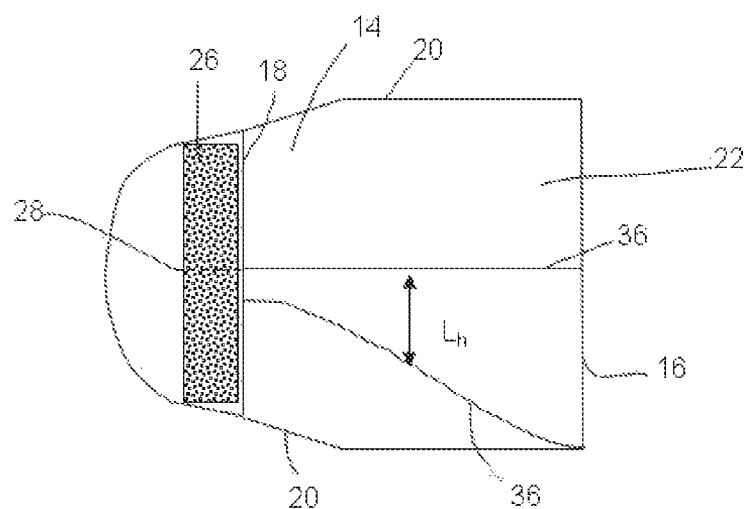

The high modulus region 22 can also be configured to focus forces on the center portion 28 of the fastening element 26 while at the same time direct tension towards one of the two connecting edges 20 near the proximal edge 16 of the extensible region 14. For instance, as shown in FIGS. 6a and 6b, the high modulus region 22 can extend from the distal edge 18 to the proximal edge 16 with the longitudinal length, $L_h$, of the high modulus region 22 increasing such that one of the borders 36 of the high modulus region 22 approaches one of the connecting edges 20 of the extensible region 14 but not both. For these embodiments, the high modulus region 22 can be made to direct tensions toward a region of the wearable article that enhances fit. For instance, in a diaper embodiment, the high modulus region 22 can be made to direct tension toward a leg region or a waist region.

The extensible region 14 of the force focused fastening member 12 may be constructed from a number of different materials. For instance, the extensible region 14 may comprise conventional elastic materials or stretch laminates. The stretch laminates may comprise a laminated structure known as live stretch, previously defined, where an elastic element is attached to a substrate while the elastic element is under strain; such that once the strain is relieved the laminate forms corrugations or gathers and exhibits a shirred structure having elastic-like properties.

Alternatively, the stretch laminate may comprise a mechanically activated stretch laminate such as a zero strain stretch laminate. Zero strain stretch laminates comprise a laminated structure which includes a first substrate, a second substrate and an elastic element. The first substrate and the second substrate, which are typically non-elastic nonwovens, are attached to the elastic element in a face to face orientation such that the elastic element is sandwiched between the first substrate and the second substrate. The laminated structure is mechanically activated enabling it to stretch. Mechanical activation refers to a process wherein the nonwoven fibers of the non-elastic substrates are broken, and/or stretched, within the nonwoven so that the nonwoven is stretched in a direction along its surfaces and can be easily expanded in that direction by partial straightening of the fibers in the nonwoven. Zero-strain elastomeric laminates are described in U.S. Pat. No. 5,143,679 issued to Weber et al., U.S. Pat. No. 5,156,793 issued to Buell et al., and U.S. Pat. No. 5,167,897 issued to Weber.

The extensible region 14 of the force focused fastening members 12 can include elastic strands or elastic films. Any suitable elastic film known in the art can be used. Suitable elastic films may comprise polypropylene, polyethylene, polyolefins, styrene-isoprene-styrene, styrene-butadiene-styrene, or combinations thereof. The basis weight of the films can range from about 10 gsm to about 100 gsm.

Suitable elastic strands can be made of a resilient elastic thermoplastic material. The elastic strands may be made from liquid elastic that is extruded through a die to achieve the desired strand elastic diameter and/or shape. The shape of the extruded elastic strands is not limited. For example, typical elastic strands have a circular cross sectional shape, but sometimes the elastic strands may have different shapes, such as a trilobal shape, or a flat (i.e., "ribbon" like) shape. Suitable elastic strand shapes include rectangles, circles, ellipses, diamonds, triangles, parallelograms, trapezoids, wedges or other sections of circles or ellipses, other polygons, or other irregular enclosed shapes. Furthermore, the thickness or diameter of the elastic strands may vary in order to accommodate a particular application. Typically, the thickness of elastic strands may be in the range of about 0.02 mm to about 1 mm and the basis weight is in the range of about 20 $g/m^2$ to about 300 $g/m^2$.

The elastic strands can be adhesively attached to the substrate, extruded onto the substrate, or printed onto the substrate. Suitable apparatuses for applying elastic strands in a longitudinal direction are described in U.S. Publication No. 2004/0238105 A1 and in U.S. application Ser. No. 10/836,944 entitled "Apparatus for Producing Elastomeric Nonwoven Laminates" filed on Apr. 30, 2004. Apparatuses for applying elastic strands in a transverse direction, an angle from the longitudinal direction, or in a curvilinear fashion are described in U.S. Publication No. US 2005-0178494 A1 entitled "Method of Placing Material Transversely on a Moving Web" filed on Feb. 13, 2004. Apparatuses for applying elastic strands in the longitudinal direction, an angle from the longitudinal direction, or in a curvilinear fashion are described in U.S. application Ser. No. 10/834,539 entitled "Extrusion Applicator Having Linear Motion Operability" filed on Apr. 29, 2004, and in U.S. application Ser. No. 10/834,503 entitled "Extrusion Applicator Having Rotational Operability" filed on Apr. 29, 2004.

Suitable apparatuses and methods for printing elastic elements in any orientation are described in U.S. Publication No. 2004-0181200A1 entitled "Variable Stretch Composites and Methods of Making the Composite" filed on Mar. 29, 2004, and in U.S. Publication No. 2004-0193133A1 entitled "Variable Stretch Composites and Methods of Making the Composite" filed on Mar. 29, 2004. For the printing of elastic strands, the individual elastic strands may be configured as lines or strands generally having widths less than about 2 mm and typically less than about 1 mm. Linear elastic strands may be configured as bands generally having widths between about 2 mm and about 20 mm and aspect ratios ranging from about 2:1 to about 100:1. Typically, the thickness of an elastic strand may be in the range of about 0.02 mm to about 5 mm and the basis weight is in the range of about 20 g/m² to about 300 g/m².

The first or second substrates forming the extensible region 14 of the force focused fastening members 12 may comprise woven materials, nonwoven materials, films, combinations of woven and/or nonwoven materials and/or films, or laminated structures having woven and/or nonwoven materials and/or films. Suitable nonwoven materials for use in accordance with the present invention may comprise fibers made of polypropylene, polyethylene, polyester, nylon, cellulose, polyamide, or combinations of such materials. Fibers of one material or fibers of different materials or material combinations may be used in the nonwovens. Suitable processes for manufacturing nonwoven materials include spunbond, spunbond meltblown spunbond (SMS), spunbond meltblown meltblown spunbond (SMMS), carded and the like. Other suitable nonwoven materials include high elongation carded (HEC) nonwovens and deep activation polypropylene (DAPP) nonwovens. Any process known in the art may be used to make the nonwovens. The basis weight of the first nonwoven and/or second nonwoven may, for example, be in the range of about 10 gsm to about 40 gsm.

The first substrate, second substrate and the elastic element may be attached by any means of attachment known in the art. Suitable attaching means and/or methods for attaching include, but are not limited to, adhesives, cohesives, thermal bonding, pressure bonding, mechanical bonding, ultrasonic bonding, coextrusion, extrusion and/or any combination of any known methods of attaching such materials.

Differences in the moduli between the high modulus region 22 and other areas of the extensible region 14 can be affected by including structural differences in the regions impacting these properties. For instance, the extensible region 14 of the force focused fastening member 12 can be mechanically activated by meshing the extensible region 14 between first and second activation rolls each of which comprises a plurality of teeth. The teeth of the first activation roll intermesh with the teeth of the second activation roll. Difference in modulus between the high modulus region 22 and other areas of the extensible region 14 can be attained by mechanically activating portions of the force focused fastening member 12 to different percentages of strain. The percentage strain experienced depends on the depth of engagement between the intermeshing teeth of the first activation roll and the teeth of the second activation roll. Activating portions of the extensible region 14 at smaller depths of engagement (e.g. shorter teeth) results in different functional characteristics as compared to portions activated at larger depths of engagement. The portions exposed to the smaller depths of engagement experience smaller percentages of strain making them less elastically extensible and thus, exhibit a larger modulus. For example, a portion of a force focused fastening member 12 which was strained to 200% may be able to elastically extend up to about three times its original length. However, a portion which was strained to 500% may be able to elastically extend up to about six times its original length.

In an alternate embodiment, the extensible region 14 of a force focused fastening member 12 may comprise a plurality of elastic elements attached to a substrate. The difference in modulus can be attained by altering the spacing of the plurality of elastic elements. For example, the spacing between each of the elastic elements in the high modulus region 22 may be about 2 mm while the spacing between each of the plurality of elastic elements in other areas of the extensible region 14 may be about 1 mm. Assuming the plurality of elastic elements in the high modulus region 22 have the same physical and chemical properties as elastic elements in other areas of the extensible region 14, the modulus can differ relative to the spacing.

In another embodiment, difference in modulus can be attained by altering the properties of a plurality of elastic elements. For instance, a plurality of elastic elements in the high modulus region 22 can have different physical or chemical properties than the physical or chemical properties of a plurality of elastic elements in other areas of the extensible region 14. For instance, a plurality of elastic elements in the high modulus region 22 may have a larger cross sectional area than a plurality of elastic elements in other areas. For example, where the elastic elements comprise elastic strands, the cross sectional area of the plurality of elastic elements in the high modulus region 22, can vary from about 0.1 mm² and less than or equal to about 0.4 mm² whereas the cross sectional area of the plurality of elastic elements in other areas of the extensible region 14 can vary from about 0.03 mm² to about 0.1 mm².

In another embodiment, the difference in modulus can be attained by providing additional elastic elements in the high modulus region 22 impacting the function of that region. For example, the extensible region 14 of the force focused fastening member 12 may comprise an elastic element in the extensible region 14. In order to increase the modulus of the high modulus region 22, an additional elastic element may be added such that its modulus is larger than the modulus of other areas.

The force focused fastening system 10 of the present invention may include fastener elements such as tape tabs, interlocking fasteners such as tabs & slots, buckles, buttons, snaps, and/or hermaphroditic fastening components, although any other known fastening means are generally acceptable. Preferably, the fastener elements include surface fasteners such as hook and loop (Velcro), adhesives, cohesives, and even magnets. Some exemplary surface fastening systems are disclosed in U.S. Pat. No. 3,848,594 entitled "Tape Fastening System for Disposable Diaper" issued to Buell on Nov. 19, 1974; U.S. Pat. No. 4,662,875 entitled "Absorbent Article" issued to Hirotsu et al. on May 5, 1987; U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; the herein before referenced U.S. Pat. No. 5,151,092 issued to Buell on Sep. 9, 1992; and U.S. Pat. No. 5,221,274 issued to Buell on Jun. 22, 1993. An exemplary interlocking fastening system is disclosed in co-pending U.S. Pat. No. 6,432,098 entitled "Absorbent Article Fastening Device" in the names of Kline et al. issued on Aug. 13, 2002. The fastening system may also provide a means for holding the article in a disposal configuration as disclosed in U.S. Pat. No. 4,963,140 issued to Robertson et al. on Oct. 16, 1990. The fastening system may also include primary and secondary fastening systems, as disclosed in U.S. Pat. No. 4,699,622 entitled "Disposable Diaper Having An Improved Side Closure" issued to Toussant et al. on Oct. 13, 1987.

The force focused fastening system 10 constructed in accordance with the present invention is adaptable to a number of wearable articles. Such wearable articles include disposable absorbent articles including diapers, pant style diapers, training pants, incontinence briefs, incontinence undergarments, absorbent inserts, diaper holders, liners, feminine hygiene garments, thermal pads, bibs and the like. Other articles include body wraps, surgical garments and packaging closures. One embodiment of a wearable article incorporating the force focused fastening system 10 of the present invention is a unitary disposable absorbent article, such as the diaper.

Figure 7:
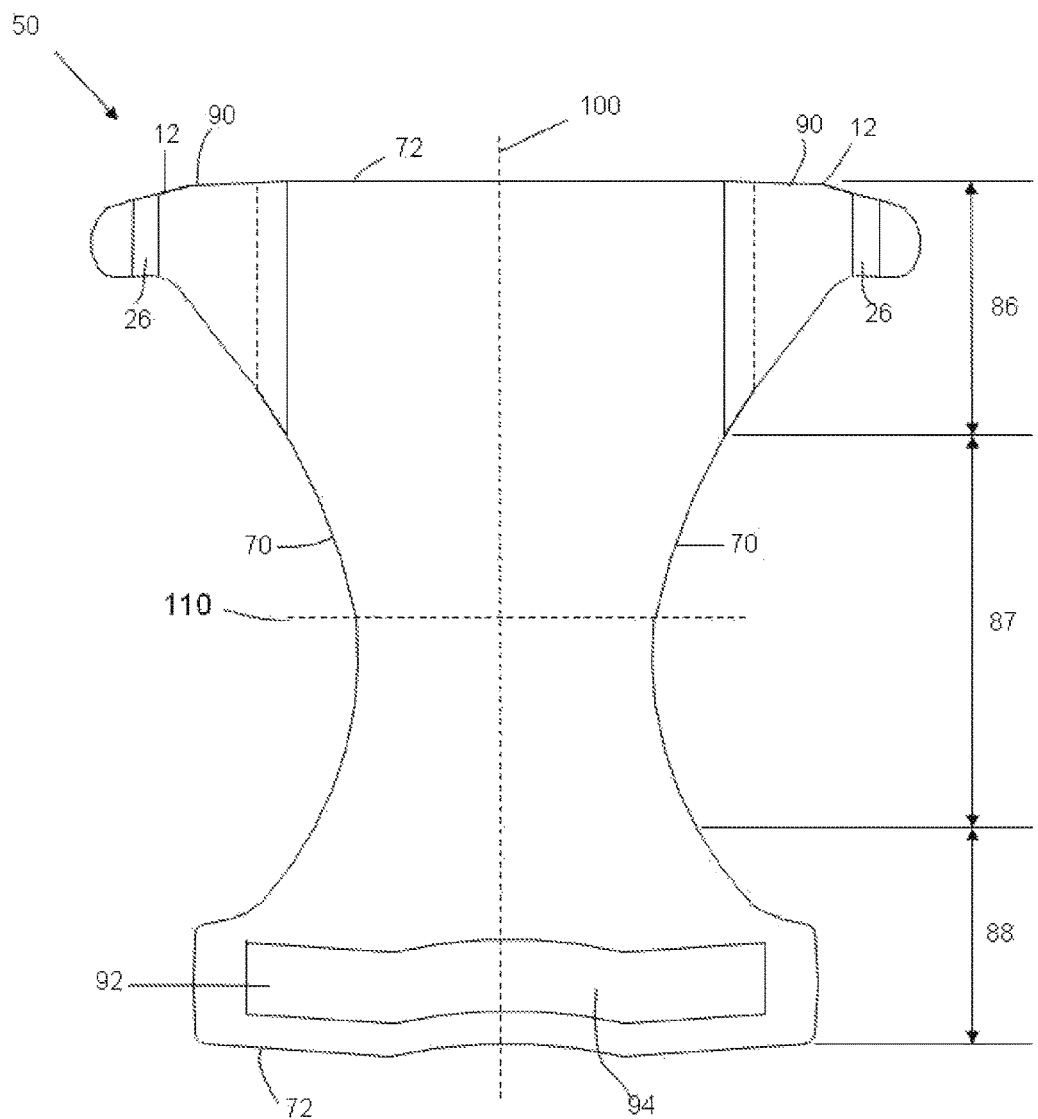
FIG. 7 is a plan view of a garment-facing surface of a disposable diaper incorporating a force focused fastening system of the present invention.

FIG. 7 is a plan view of the diaper 50 including first fastening members 90 and a second fastening member 92 where the first fastening members 90 comprises a force focused fastening member 12 including fastener element 26 and the second fastening member 92 comprises a landing zone 94. For this embodiment, both the fastener elements 26 and the landing zone 94 can comprise a hook or loop fastening components. The diaper 50 is shown in a flat-out state with the garment facing side facing the viewer. The diaper 50 has a first waist region 86, a second waist region 88 opposed to the first waist region 86 and a crotch region 87 located between the first waist region 86 and the second waist region 88. The periphery of the diaper 50 is defined by the outer edges of the diaper 50 in which longitudinal edges 70 run generally parallel to the longitudinal centerline 100 of the diaper 50 and end edges 72 run between the longitudinal edges 70 generally parallel to the lateral centerline 110 of the diaper 50.

Figure 8:
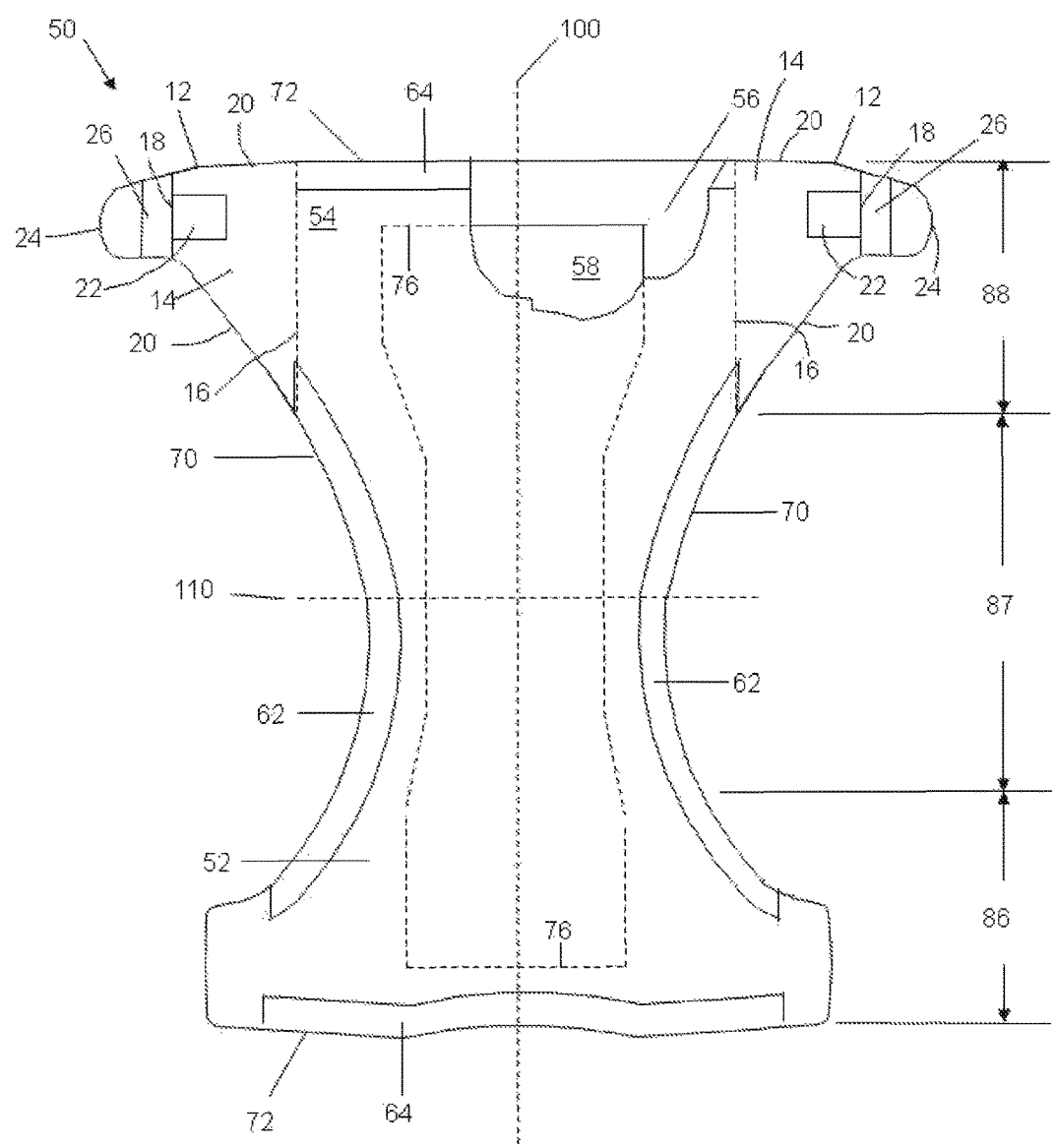
FIG. 8 is a plan view of a body-facing surface of a disposable diaper incorporating a force focused fastening system of the present invention.

In FIG. 8, the diaper 50 is shown in a flat-out state with the portion of the diaper 50 which faces the wearer oriented towards the viewer. As shown in FIG. 8, portions of the structure are cut-away to more clearly show the construction of the diaper 50. The diaper 50 comprises a liquid pervious topsheet 54; a liquid impervious backsheet 56; an absorbent core 58 which is preferably positioned between at least a portion of the topsheet 54 and the backsheet 56; extensible leg cuffs 62, and elastic waist features 64. The chassis 52 of the diaper 50 comprises the main body of the diaper 50 and includes the topsheet 54 and/or the backsheet 56 and at least a portion of the absorbent core 58. While the topsheet 54, the backsheet 56, the absorbent core 28, force focused fastening members 12 and other aforementioned constituents may be assembled in a variety of well known configurations, preferred diaper configurations are described generally in U.S. Pat. No. 3,860,003 entitled "Contractible Side Portions for Disposable Diaper" issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; U.S. Pat. No. 5,580,411 entitled "Zero Scrap Method for Manufacturing Side Panels for Absorbent Articles" issued to Nease et al. on Dec. 3, 1996; and U.S. Pat. No. 6,004,306 entitled "Absorbent Article With Multi-Directional Extensible Side Panels" issued to Robles et al. on Dec. 21, 1999.

The force focused fastening members 12 can have a number of different sizes and shapes, but for this embodiment, the force focused fastening members 12 preferably have a trapezoidal shape. The extensible region 14 of the force focused fastening members 12 can be elastic or extensible to provide a more comfortable and contouring fit by initially conformably fitting the diaper 50 to the wearer and sustaining this fit throughout the time of wear. As such, the force focused fastening members 12 can be made to provide a sustained fit well past when the diaper 50 has been loaded with exudates by allowing the sides of the diaper 50 to expand and contract. The force focused fastening members 12 can also be made to provide more effective application of the diaper 50 because even if one force focused fastening member 12 is pulled farther than the other during application, the diaper 50 will "self-adjust" during wear.

The force focused fastening members 12 may comprise a separate element affixed to the chassis 52, or can be constructed as an extension of other elements of the diaper such as the backsheet 56 or the topsheet 54, preferably both the topsheet 54 and the backsheet 56. In the embodiment shown in FIG. 7, the force focused fastening members 12 each comprise a separate web joined to the chassis 52 in the second waist region 38 and extend laterally outwardly beyond the longitudinal edges 70. The force focused fastening members 12 comprise an extensible region 14 having a proximal edge 16 and a distal edge 18 and two connecting edges 20. A first connecting edge 20 positioned adjacent the end edge 72 of the diaper 50, a second connecting edge 20 positioned away from the first end edge 72 towards the lateral centerline 110. The proximal edge 16 is attached to the longitudinal edge 70, and the distal edge 18 positioned laterally outwardly from the longitudinal edge 70. The proximal edge 16 may be contiguous with the longitudinal edge 70, preferably the proximal edge 16 is positioned laterally inwardly of the longitudinal edge 70. The force focused fastening members 12 includes an end region 24 extending from the distal edge 18 of the extensible region 14. The end region 24 may be elastic or nonelastic. Fastener element 26 is attached to the end region 24.

While the diaper 50 shown in FIG. 7 and FIG. 8 has the force focused fastening members 12 disposed in the second waist region 88, the diaper 50 may be provided with force focused fastening members 12 disposed in the first waist region 86 or in both the first waist region 86 and the second waist region 88. The force focused fastening members 12 may be constructed in any suitable configurations. Examples of diapers with side panels having extensible regions are disclosed in U.S. Pat. No. 4,857,067, entitled "Disposable Diaper Having Shined Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; the herein before referenced U.S. Pat. No. 5,151,092 issued to Buell on Sep. 9, 1992; U.S. Pat. No. 5,221,274 issued to Buell on Jun. 22, 1993; U.S. Pat. No. 5,669,897 issued to LaVon, et al. on Sep. 23, 1997 entitled "Absorbent Articles Providing Sustained Dynamic Fit"; and U.S. Pat. No. 6,004,306 entitled "Absorbent Article With Multi-Directional Extensible Side Panels" issued to Robles et al. on Dec. 21, 1999.

The diaper 50 may comprise at least one elastic waist feature 64 that helps to provide improved fit and containment. The elastic waist feature 64 is generally intended to elastically expand and contract to dynamically fit the wearer's waist. The elastic waist feature 64 preferably extends at least longitudinally outwardly from at least one waist edge 76 of the absorbent core 58 and generally forms at least a portion of the end edge 72 of the diaper 50. Disposable diapers are often constructed so as to have two elastic waist features, one positioned in the first waist region 86 and one positioned in the second waist region 88. Further, while the elastic waist feature 64 or any of its constituent elements may comprise one or more separate elements affixed to the diaper 50, the elastic waist feature 64 may be constructed as an extension of other elements of the diaper 50, such as the backsheet 56, the topsheet 54, or both the backsheet 56 and the topsheet 54.

The elastic waist feature 64 in the second waist region 88 provides an extensible member that provides a more comfortable and contouring fit by initially conformably fitting the diaper to the wearer and sustaining this fit throughout the time of wear well past when the diaper has been loaded with exudates since the extensible waist feature, particularly in the back portion of the diaper allows the diaper to expand and, preferably, to contract. Further, the elastic waist feature 64 in the second waist region 88 develops and maintains wearing forces (tensions) that enhance the tensions developed and maintained by the closure system to maintain the diaper on the wearer and enhance the fit of the diaper 50 about the waist of the wearer. The elastic waist feature 64 in the second waist region 88 further provides more effective application of the diaper 50 since even if the caregiver pulls one side of the elastic waist feature farther than the other during application (asymmetrically), the diaper will "self-adjust" during wear.

The elastic waist feature 64 may be attached to the outer, garment facing surface of the backsheet 56; the body facing surface of the topsheet 54 or both. In addition the elastic waist feature 64 may be attached between the topsheet 54 and the backsheet 56, or wrapped around the end edges 72 of the diaper 50 and attached to both the body-facing surface of the topsheet 54 and the garment-facing surface of the backsheet 56.

The elastic waist feature 64 may be constructed in a number of different configurations. For instance, the elastic waist feature 64 may comprise a laminate structure consisting of a single layer of nonwoven with an elastomeric material attached covering a full width dimension of the nonwoven or only a portion of the width. The elastomeric material may include an elastomer extruded onto the nonwoven or a film that is glued to the nonwoven. Alternatively, the elastic waist feature 64 may comprise a laminate structure comprising two layers of nonwoven with elastomeric strands disposed therebetween covering the full width of the laminate or only a portion of the width. In addition, the elastic waist feature 64 may be constructed according to U.S. Pat. No. 4,515,595 issued to Kievit et al. on May 7, 1985; U.S. Pat. No. 4,710,189 issued to Lash on Dec. 1, 1987; U.S. Pat. No. 5,151,092 issued to Buell on Sep. 9, 1992; and U.S. Pat. No. 5,221,274 issued to Buell on Jun. 22, 1993. Other suitable waist configurations may include waist cap features such as those described in U.S. Pat. No. 5,026,364 issued to Robertson on Jun. 25, 1991 and U.S. Pat. No. 4,816,025 issued to Foreman on Mar. 28, 1989.

The diaper 50 can also comprise extensible leg cuffs 62 for providing improved containment of liquids and other body exudates. Each extensible leg cuff 62 may comprise several different embodiments for reducing the leakage of body exudates in the leg regions. (The leg cuff can be and is sometimes also referred to as leg bands, leg flaps, barrier cuffs, or elastic cuffs.) The extensible leg cuffs 62 may be attached to the outer, garment facing surface of the backsheet; the body facing surface of the topsheet or both. In addition, the extensible leg cuffs 62 may be attached between the topsheet and the backsheet, or wrapped around the longitudinal edges 70 of the diaper 50 and attached to both the body-facing surface of the topsheet 54 and the garment-facing surface of the backsheet 56.

Like the elastic waist feature 64, the extensible leg cuffs 62 may be constructed in a number of different configurations. For instance, the extensible leg cuffs 62 may comprise a laminate structure consisting of a single layer of nonwoven with an elastomeric material attached covering a full width dimension of the nonwoven or only a portion of the width. The elastomeric material may include an extruded elastic strand laminate comprising prestrained extruded elastic strands laminated to a nonwoven or a film that is subsequently glued to the garment facing surface of the backsheet along the longitudinal edges 70 of the diaper 50 and allowed to relax to form a shirred or corrugated structure. Alternatively, the extensible leg cuffs 62 may comprise a laminate structure comprising two layers of nonwoven with prestrained extruded elastic strands laminated between the two layers of nonwoven covering the full width of the laminate or only a portion of the width. The laminate structure can be subsequently glued to the garment facing surface of the backsheet along the longitudinal edges 70 of the diaper 50 while in the prestrained condition so that a shirred or corrugated structure is formed once tension is removed from the laminate allowing it to relax. In addition, the extensible leg cuffs 62 may comprise a prestrained elastic strand or strands bonded in a prestrained condition between a portion of the backsheet or topsheet that is folded over.

In addition, the extensible leg cuffs 62 may be constructed according to one or more of the patents described hereunder. U.S. Pat. No. 3,860,003 entitled "Contractable Side Portions For a Disposable Diaper", issued to Buell on Jan. 14, 1975, describes a disposable diaper providing a contractible leg opening having a leg flap and one or more elastic members to provide an elasticized leg cuff (gasketing cuff). U.S. Pat. No. 4,909,803 entitled "Disposable Absorbent Article Having Elasticized Flaps" issued to Aziz & Blaney on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff. U.S. Pat. No. 4,704,115 entitled "Disposable Waste Containment Garment" issued to Buell on Nov. 3, 1987, discloses a disposable diaper or incontinent garment having side-edge-leakage-guard gutters configured to contain free liquids within the garment. U.S. Pat. No. 5,032,120 entitled "Disposable Absorbent Article Having Improved Leg Cuffs" issued to Freeland & Allen on Jul. 16, 1991, discloses an absorbent article having leg cuffs having a relatively low ultimate contact force at relatively high elongations accomplished, for example, by low contact force differential material. U.S. Pat. No. 5,087,255 entitled "Absorbent Article Having Inflected Barrier Cuffs" issued to Sims on Feb. 11, 1992, discloses an absorbent article having inflected barrier cuffs with the distal edge positioned outboard of the proximal edge in one waist region and inboard in the other to provide better fit about the hips/buttocks.

The extensible regions 14 of the force focused fastening members 12 can be made to further enhance fit of the diaper about a wearer by coordinating with the leg and waist regions of the diaper. For instance, the elastic waist feature 64 in the second waist region 88 can be made to extend into one or both of the force focused fastening members 12 partially or fully covering the region above the high modulus region 22 in one or both of the force focused fastening members 12. Similarly, the extensible leg cuffs 32 can be made to extend into one or both of the force focused fastening members 12 partially or fully covering the region below the high modulus region 22 in one or both of the force focused fastening members 12. Alternatively, the high modulus region 22 of each of the force focused fastening members 12 can be oriented to direct tension into the leg and/or waist regions 62, 64.

Other components of the chassis 52 include the backsheet 56, the topsheet 54 and the core 58. The backsheet 56 is generally that portion of the diaper 50 positioned adjacent garment facing surface of the absorbent core 58 which prevents the exudates absorbed and contained therein from soiling articles which may contact the diaper 50, such as bed sheets and undergarments. In preferred embodiments, the backsheet 56 is impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Corporation, based in Richmond, Va., and sold under the trade name CPC2 film. Other suitable backsheet materials may include breathable materials which permit vapors to escape from the diaper 50 while still preventing exudates from passing through the backsheet 56. Exemplary breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va. and sold under the designation EXAIRE, and monolithic films such as manufactured by Clopay Corporation, Cincinnati, Ohio under the name HYTREL blend P18-3097. Some breathable composite materials are described in greater detail in PCT Application No. WO 95/16746 published on Jun. 22, 1995 in the name of E. I. DuPont; U.S. Pat. No. 5,938,648 issued on Aug. 17, 1999 to LaVon et al.; U.S. Pat. No. 5,865,823 issued on Feb. 2, 1999 in the name of Curro; and U.S. Pat. No. 5,571,096 issued to Dobrin et al. on Nov. 5, 1996.

The backsheet 56, or any portion thereof, may be elastically extensible in one or more directions. In one embodiment, the backsheet 56 may comprise a structural elastic-like film ("SELF") web. A structural elastic-like film web is an extensible material that exhibits an elastic-like behavior in the direction of elongation without the use of added elastic materials and is described in more detail in U.S. Pat. No. 5,518,801 entitled "Web Materials Exhibiting Elastic-Like Behavior" issued to Chappell, et al. on May 21, 1996. In alternate embodiments, the backsheet 56 may comprise elastomeric films, foams, strands, or combinations of these or other suitable materials with nonwovens or synthetic films.

The backsheet 56 may be joined to the topsheet 54, the absorbent core 58 or any other element of the diaper 50 by any attachment means known in the art. For example, the attachment means may include a uniform continuous layer of adhesive, a patterned layer of adhesive, or an array of separate lines, spirals, or spots of adhesive. One preferred attachment means comprises an open pattern network of filaments of adhesive as disclosed in U.S. Pat. No. 4,573,986 entitled "Disposable Waste-Containment Garment", which issued to Minetola et al. on Mar. 4, 1986. Other suitable attachment means include several lines of adhesive filaments which are swirled into a spiral pattern, as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Adhesives which have been found to be satisfactory are manufactured by H. B. Fuller Company of St. Paul, Minn. and marketed as HL-1620 and HL 1358-XZP. Alternatively, the attachment means may comprise heat bonds, pressure bonds, ultrasonic bonds, dynamic mechanical bonds, or any other suitable attachment means or combinations of these attachment means as are known in the art.

The topsheet 54 is preferably positioned adjacent body surface of the absorbent core 58 and may be joined thereto and/or to the backsheet 56 by any attachment means known in the art. Suitable attachment means are described above with respect to means for joining the backsheet 56 to other elements of the diaper 50. In one preferred embodiment of the present invention, the topsheet 54 and the backsheet 56 are joined directly to each other in some locations and are indirectly joined together in other locations by directly joining them to one or more other elements of the diaper 50.

The topsheet 54 is preferably compliant, soft-feeling, and non-irritating to the wearer's skin. Further, at least a portion of the topsheet 54 is liquid pervious, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers), synthetic fibers (e.g., polyester or polypropylene fibers), or a combination of natural and synthetic fibers. If the topsheet 54 includes fibers, the fibers may be spunbond, carded, wet-laid, meltblown, hydroentangled, or otherwise processed as is known in the art. One suitable topsheet 54 comprising a web of staple-length polypropylene fibers is manufactured by Veratec, Inc., a Division of International Paper Company, of Walpole, Mass. under the designation P-8.

Suitable formed film topsheets are described in U.S. Pat. No. 3,929,135, entitled "Absorptive Structures Having Tapered Capillaries" issued to Thompson on Dec. 30, 1975; U.S. Pat. No. 4,324,246 entitled "Disposable Absorbent Article Having A Stain Resistant Topsheet" issued to Mullane, et al. on Apr. 13, 1982; U.S. Pat. No. 4,342,314 entitled "Resilient Plastic Web Exhibiting Fiber-Like Properties" issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression" issued to Ahr, et al. on Jul. 31, 1984; and U.S. Pat. No. 5,006,394 "Multilayer Polymeric Film" issued to Baird on Apr. 9, 1991. Other suitable topsheets may be made in accordance with U.S. Pat. Nos. 4,609,518 and 4,629,643 issued to Curro et al. on Sep. 2, 1986 and Dec. 16, 1986, respectively. Such formed films are available from The Procter & Gamble Company of Cincinnati, Ohio as "DRI-WEAVE" and from Tredegar Corporation, based in Richmond, Va., as "CLIFF-T."

Preferably, at least a portion of the topsheet 54 is made of a hydrophobic material or is treated to be hydrophobic in order to isolate the wearer's skin from liquids contained in the absorbent core 58. If the topsheet 54 is made of a hydrophobic material, preferably at least a portion of the upper surface of the topsheet 54 is treated to be hydrophilic so that liquids will transfer through the topsheet more rapidly. The topsheet 54 can be rendered hydrophilic by treating it with a surfactant or by incorporating a surfactant into the topsheet. Suitable methods for treating the topsheet 54 with a surfactant include spraying the topsheet 54 material with the surfactant and/or immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al. on Jan. 29, 1991 and U.S. Pat. No. 4,988,345 entitled "Absorbent Articles with Rapid Acquiring Absorbent Cores" issued to Reising on Jan. 29, 1991. A more detailed discussion of some suitable methods for incorporating a surfactant in the topsheet 54 can be found in U.S. Statutory Invention Registration No. H1670 published on Jul. 1, 1997 in the names of Aziz et al. Alternatively, the topsheet 54 may include an apertured web or film which is hydrophobic. This may be accomplished by eliminating the hydrophilizing treatment step from the production process and/or applying a hydrophobic treatment to the topsheet 54, such as a polytetraflouroethylene compound like SCOTCHGUARD or a hydrophobic lotion composition, as described below. In such embodiments, it is preferred that the apertures be large enough to allow the penetration of aqueous fluids like urine without significant resistance.

The absorbent core 58 may comprise any absorbent material which is generally compressible, conformable, non-irritating to the wearer's skin, and capable of absorbing and retaining liquids such as urine and other certain body exudates. The absorbent core 58 may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The configuration and construction of the absorbent core 58 may also be varied (e.g., the absorbent core(s) or other absorbent structure(s) may have varying caliper zones, hydrophilic gradient(s), a superabsorbent gradient(s), or lower average density and lower average basis weight acquisition zones; or may comprise one or more layers or structures). Exemplary absorbent structures for use as the absorbent core 58 are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,834,735 entitled "High Density Absorbent Members Having Lower Density and Lower Basis Weight Acquisition Zones" issued to Alemany et al. on May 30, 1989; U.S. Pat. No. 4,888,231 entitled "Absorbent Core Having A Dusting Layer" issued to Angstadt on Dec. 19, 1989; U.S. Pat. No. 5,137,537 entitled "Absorbent Structure Containing Individualized, Polycarboxylic Acid Crosslinked Wood Pulp Cellulose Fibers" issued to Herron et al. on Aug. 11, 1992; U.S. Pat. No. 5,147,345 entitled "High Efficiency Absorbent Articles For Incontinence Management" issued to Young et al. on Sep. 15, 1992; U.S. Pat. No. 5,342,338 entitled "Disposable Absorbent Article For Low-Viscosity Fecal Material" issued to Roe on Aug. 30, 1994; U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; and U.S. Pat. No. 5,625,222 entitled "Absorbent Foam Materials For Aqueous Fluids Made From High Internal Phase Emulsions Having Very High Water-To-Oil Ratios" issued to DesMarais et al. on Jul. 22, 1997.

Force Focusing Method

All testing is to occur in conditions controlled to 22° C.±2° C., 50% Relative Humidity±10% Relative Humidity. Samples are conditioned at these conditions at least 24 hours prior to testing. All distance measures made to the nearest 0.1 mm, using a calibrated caliper or image analysis system.

Figure 9:
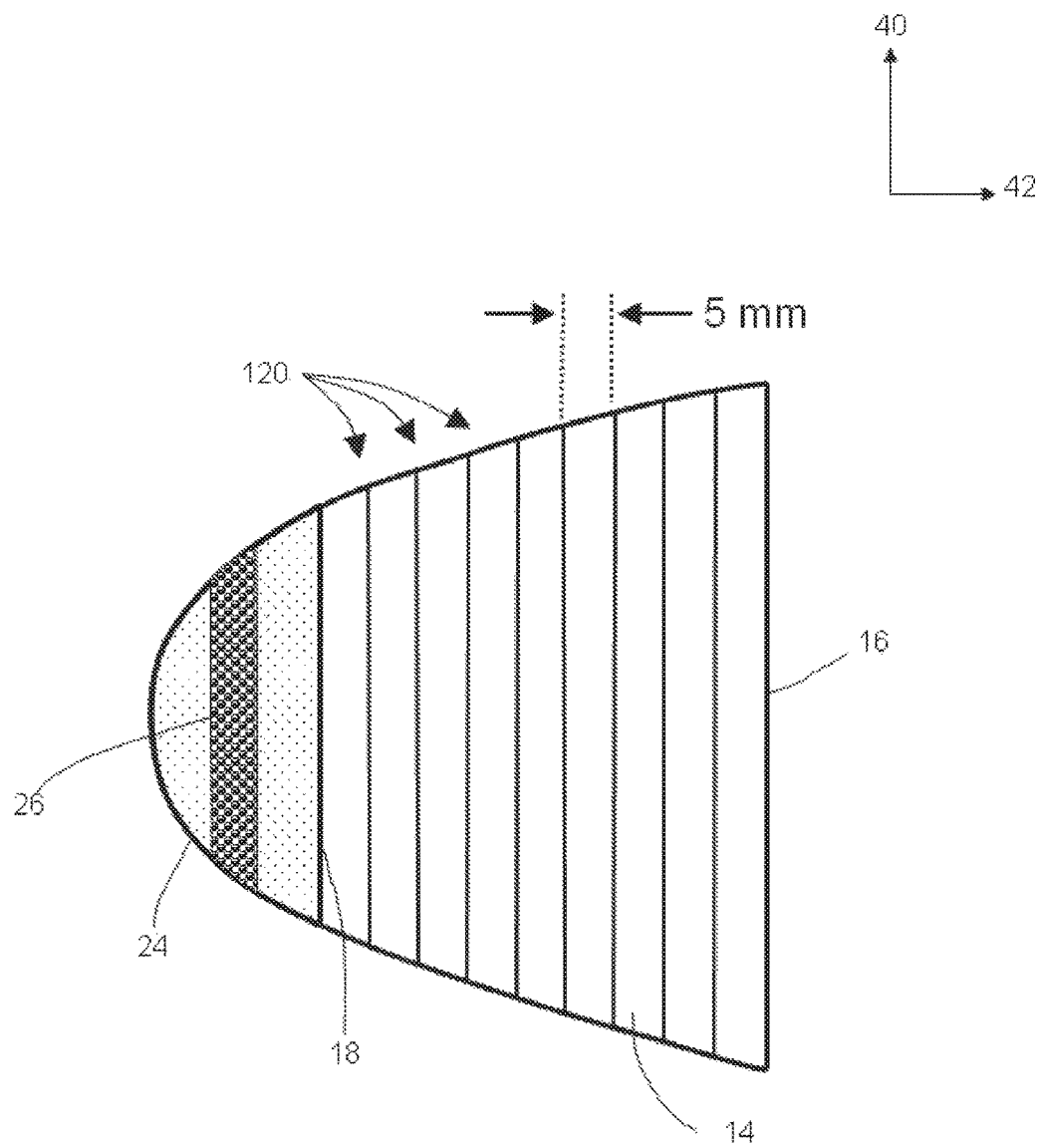
FIG. 9 is a plan view of the force focused fastening member used in the force focusing test method showing grid lines.
Figure 10A:
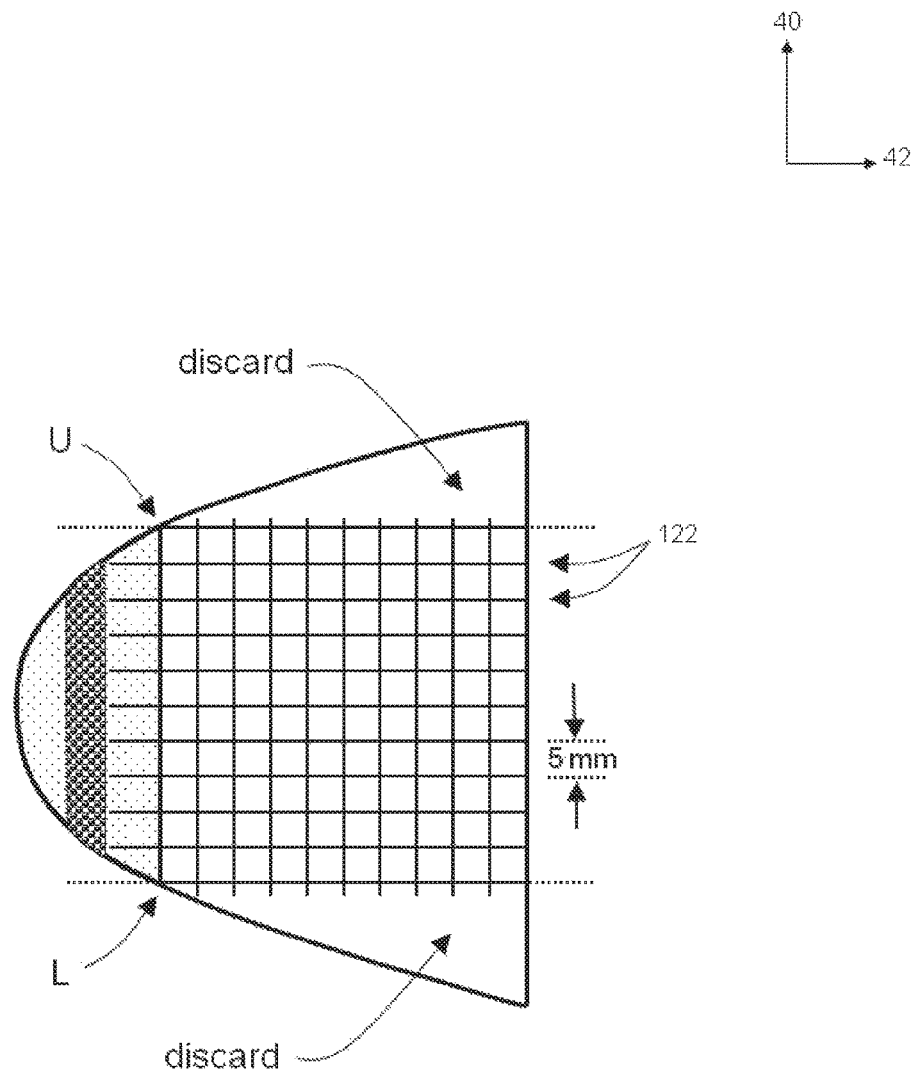
FIG. 10a is a plan view of the force focused fastening member used in the force focusing test method showing the cut lines.
Figure 10B:
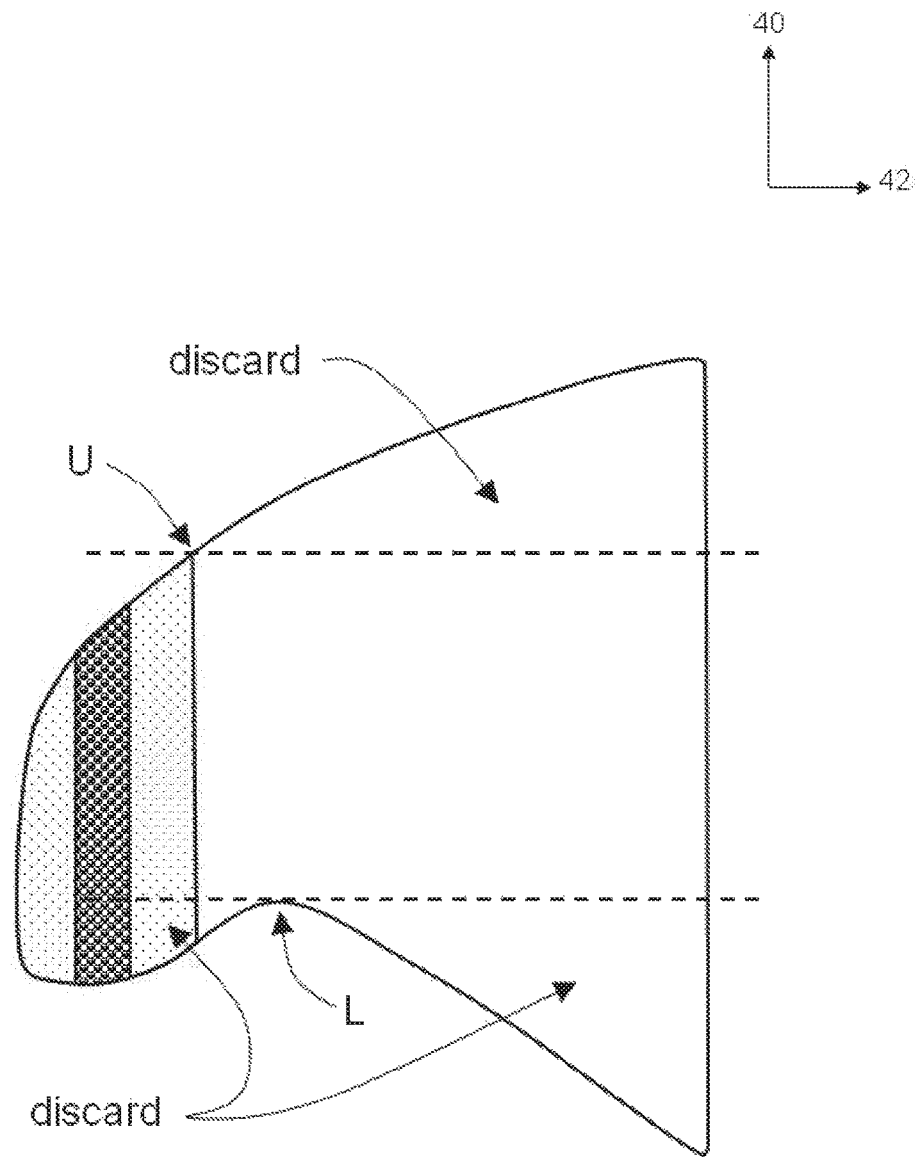
FIG. 10b is a plan view of the force focused fastening member used in the force focusing test method showing the portion to be tested.

Creation of Sample Strips
1. Procure a representative fastening member and identify longitudinal direction 40 and transverse directions 42. Extensibility is to be in at least the transverse direction 42.
2. As shown in FIG. 9, mark a plurality of grid lines 120 on the fastening member, each grid line 120 parallel to (within ±2 degrees of) the longitudinal direction 40, with a first grid line 120 being adjacent the fastening element 26 and the last grid line being adjacent to and about 5 mm from the end of the sample proximal edge 16.
   a. The grid lines 120 are to spaced 5 mm apart.
   b. Each grid line 120 is to be no more than 1 mm wide.
   c. The color of the grid lines 120 is to be of sufficient contrast in color to be readily distinguishable from the background substrate material color.
   d. The grid lines 120 are to be of a material that does not significantly interfere with the extension of the extensible region, such as ink from a fine-point marker.
   e. The sample is not to be extended during steps 1 and 2
3. Prepare the sample to be cut laterally into a plurality of strips:
   a. If the fastening member's extensible region is not a rectangle, cut it into a rectangle as shown in FIGS. 10a and 10b (grid lines not shown for simplicity). The uppermost edge is to coincide with either a point U along the innermost upper edge of the end region or the uppermost location that allows a continuous line to be cut. The lowermost edge is to coincide with either a point L along the innermost lower edge of the end region or the lowermost location that allows a continuous line to be cut.
   b. Mark locations for cut lines 122 in 5 mm increments, beginning 5 mm from the uppermost edge of the sample (FIG. 10a), with each cut line 122 parallel to the uppermost edge of the initial rectangle.
   c. Mark each strip with an identifying code to identify longitudinal location within the fastening member.
   d. Cut the sample along the cut lines to create sample strips.
   e. If the strip adjacent the lowermost edge is <5 mm, discard it.
4. Create a grid worksheet, with the same number of columns and rows as have been constructed on the sample (see FIG. 12a).

Measurement of % Extensions of Sample Strips
1. Mount a digital camera (minimum 4 mega pixel, with optical zoom; a suitable camera is the Kodak EasyShare DX6490 available from the Eastern Kodak Co., Rochester, N.Y.) perpendicular to the sample's surface (as defined by the longitudinal and lateral directions of the sample in the grips) on a tripod 50 cm away from the sample surface, with the sample centered in the camera's field of vision and the camera in focus. To preserve the image quality, only use the camera's optical zoom, not its digital zoom. The camera can not be moved or its magnification altered throughout the experiment.
2. The sample strips are extended in their original transverse direction 42 (FIG. 10a) using a constant rate of extension tensile tester with computer interface (a suitable instrument is the MTS Alliance using Testworks 4.0 Software, as available from MTS Systems Corp., Eden Prairie, Minn.). The tensile tester is fitted with a 10 N load cell and two 2.54 cm×2.54 cm rubber faced grips are used for both the stationary and movable pneumatic jaws.

Figure 11A:
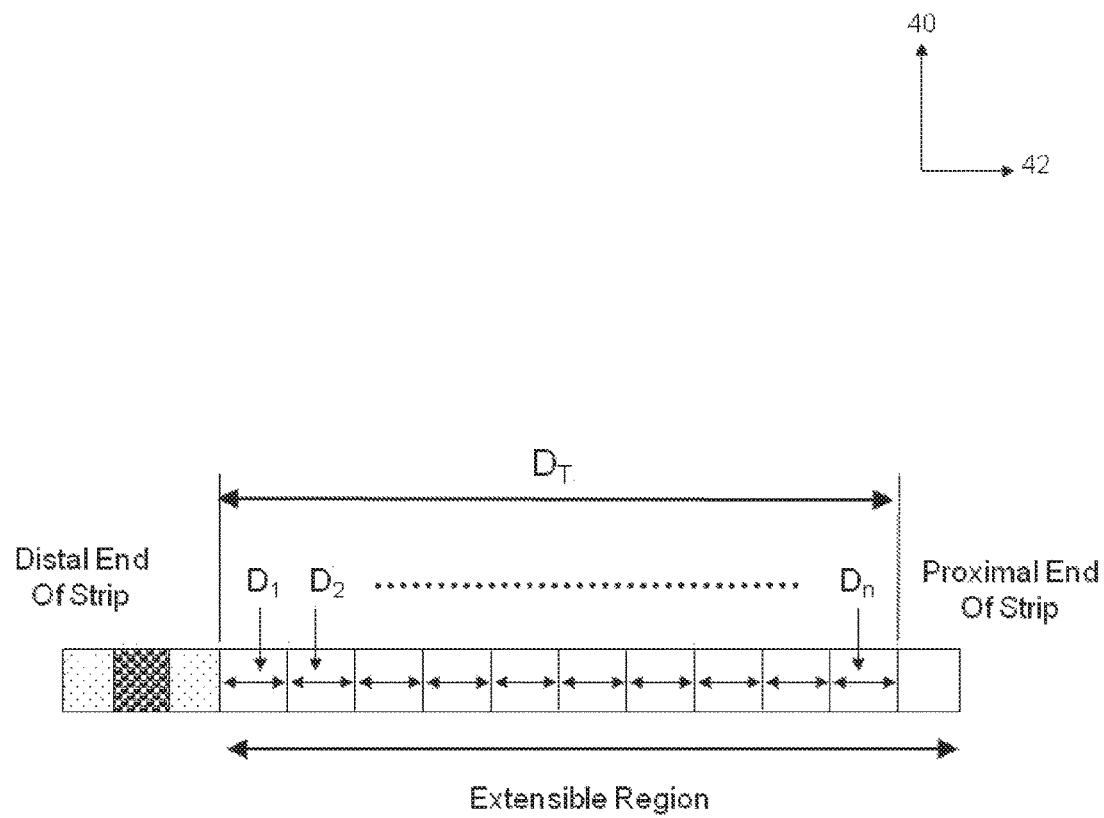
FIG. 11a is a plan view of a strip of the force focused fastening member used in the force focusing test method.
Figure 11B:
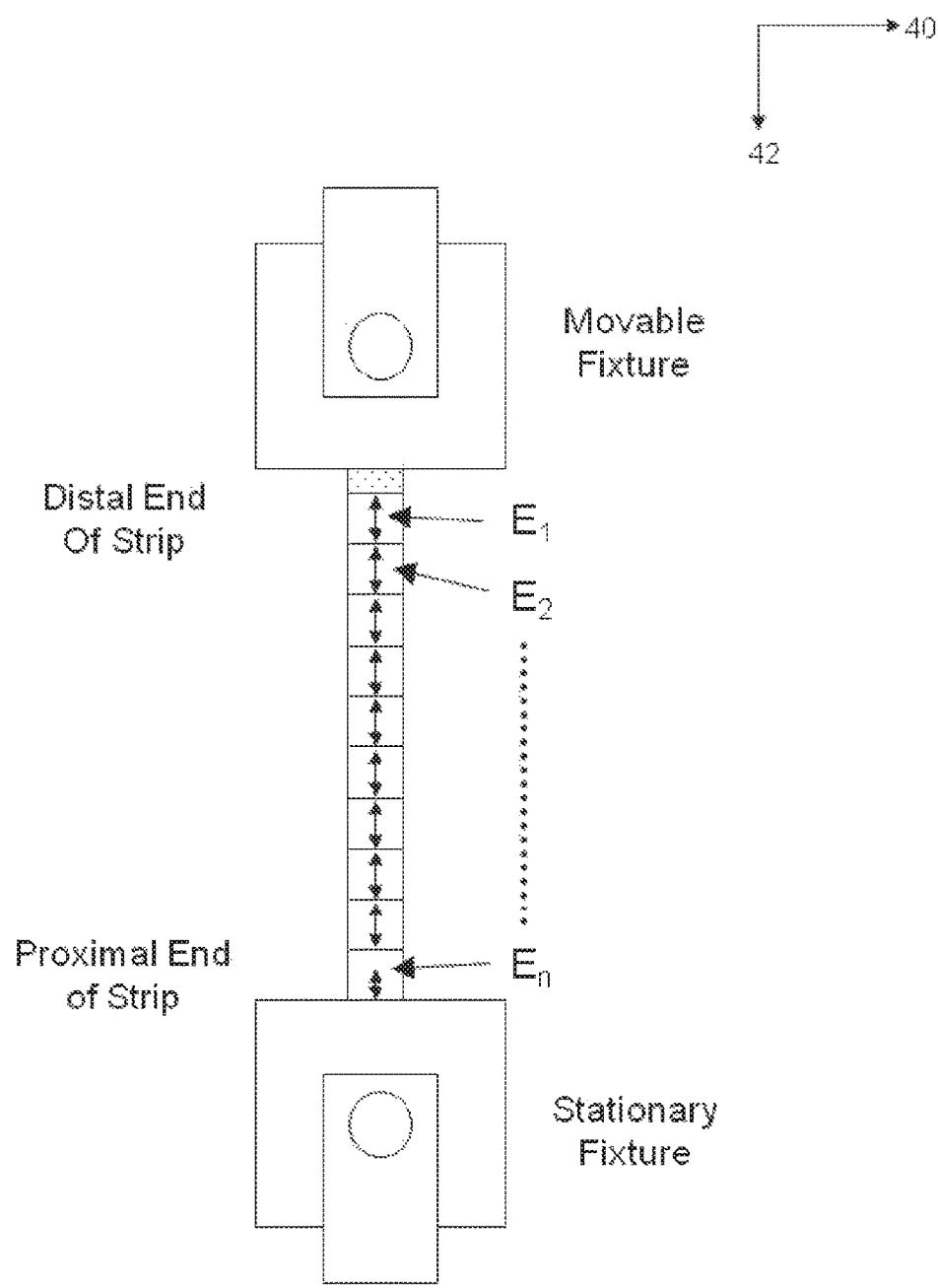
FIG. 11b is a plan view of the strip in FIG. 11a in the test set up.

3. Measure the initial, unextended distance $D_T$ from the first grid line to the last grid line as shown in FIG. 11a. Set the gage length of the tensile tester to that distance $D_T$, and reset the crosshead to zero.
4. Secure the distal end of the sample into the upper grips of the tensile tester, with the face of the grip aligned with the first grid line from step 2. At least 5 mm (in the lateral direction) of the end region is placed in the grips. Move the upper grip closer to the lower grip to allow the proximal end to be placed in the lower grip without extending the sample.
5. Secure the proximal end into the lower grip of the tensile tester (FIG. 11b), with the face of the grip aligned with the last grid line from step 2.
6. Zero the load cell of the tensile tester, and return the cross head to its original gage length (i.e. zero position of crosshead).
7. Within 1 second of reaching the defined gage length (distance $D_T$), take a photograph of the unextended sample.
8. Move the upper fixture away from the lower fixture at a rate of 127 mm/minute until a force of 0.5 N/cm is applied to the sample (where Newtons refers to the actual force applied and is normalized to the longitudinal width of the sample in cm). Within 1 second of reaching the target load, take a second photograph of the extended sample.
9. Move the upper fixture away from the lower fixture at a rate of 127 mm/minute until a force of 1.5 N/cm is applied to the sample. Within 1 second of reaching the target force, take a third photograph of the extended sample.
10. Move the upper fixture away from the lower fixture at a rate of 127 mm/minute until a force of 4.0 N/cm is applied to the sample. Within 1 second of reaching the target load, take a fourth photograph of the extended sample.
11. Print all four photographs at identical magnification. The scale of the pictures is to be such that the size of the sample in the photograph is between 100% and 150% of actual size. The first picture can be used to determine the scale by comparing grip spacing in the photograph to value $D_T$.
12. From the first picture, measure and record the initial, unextended line-to-line distances ($D_1$ to $D_n$) to the nearest 0.1 mm. The distance is to be measured in the longitudinal center of the sample (FIG. 11a) directly parallel to the lateral direction.
13. From the second picture, measure and record the extended line-to-line distances ($E_1$ to $E_n$) at the first target load to the nearest 0.1 mm. The distance is to be measured in the longitudinal center of the sample.
14. From the third picture, measure and record the extended line-to-line distances ($E_1$ to $E_n$) at the second target load to the nearest 0.1 mm. The distance is to be measured in the longitudinal center of the sample.
15. From the fourth picture, measure and record the extended line-to-line distances ($E_1$ to $E_n$) at the third target load to the nearest 0.1 mm. The distance is to be measured in the longitudinal center of the sample.
16. For each applied force, calculate % Extension line-to-line, for each pair of adjacent lines at each applied force, with % Extension being:

% Extension=$100*(E_i-D_i)/(D_i)$, when $i=1$ to $n$

Figure 12A:
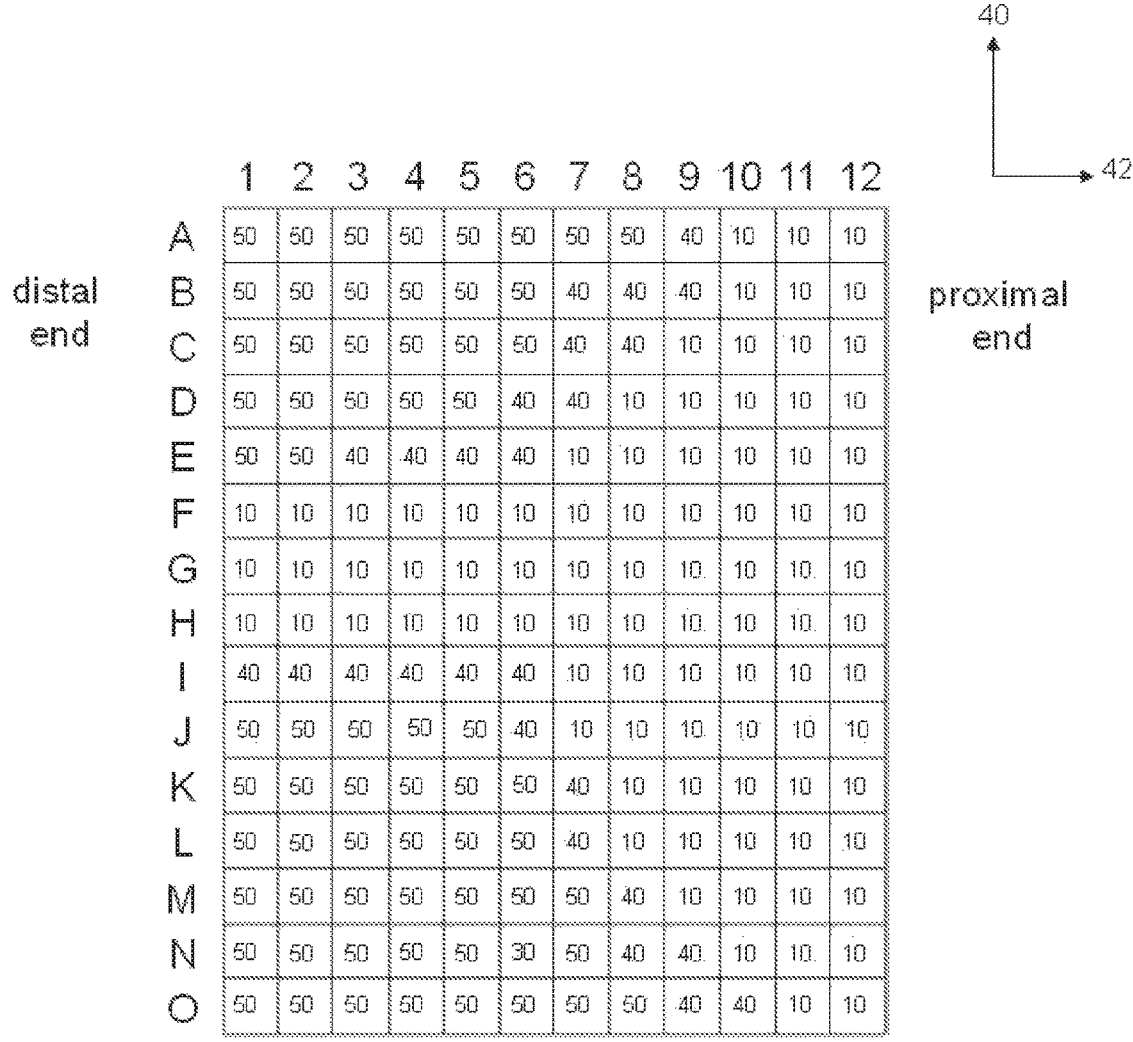
FIG. 12a is a grid worksheet used in the force focused test method.

17. Record the calculated % Extension for each cell on a grid worksheet (such as shown in FIG. 12a) for each applied force.
18. Repeat steps 4-12 for each strip of the fastening member.

Evaluation of % Extension Grids
1. Evaluate each of the three grid worksheets (one worksheet per each applied force) to determine which one contains the greatest range of % extension.
   a. Select a grid worksheet.
   b. Compare the % extension values in the upper most horizontal row of the grid. The greatest % extension value in this row is $E_{max\ upper}$.
   c. Compare the % extension values in the lower most horizontal row of the grid. The greatest % extension value in this row is $E_{max\ lower}$.
   d. Compare the % extension values in all remaining horizontal rows of the grid. The least % extension value in any of these rows is $E_{min\ center}$.
   e. Calculate the differences in % extensions using the following:

Difference in % Extension(upper vs. center)=$100*(E_{max-upper}-E_{min\ center})/E_{min\ center}$ Difference in % Extension(lower vs. center)=$100*(E_{max\ lower}-E_{min\ center})/E_{min\ center}$ f. Repeat steps 1a through 1e for each of the three grid worksheets.
2. Select the grid worksheet with the greatest difference in % extension as indicated for either the above equations for further grid analysis.

Figure 12B:
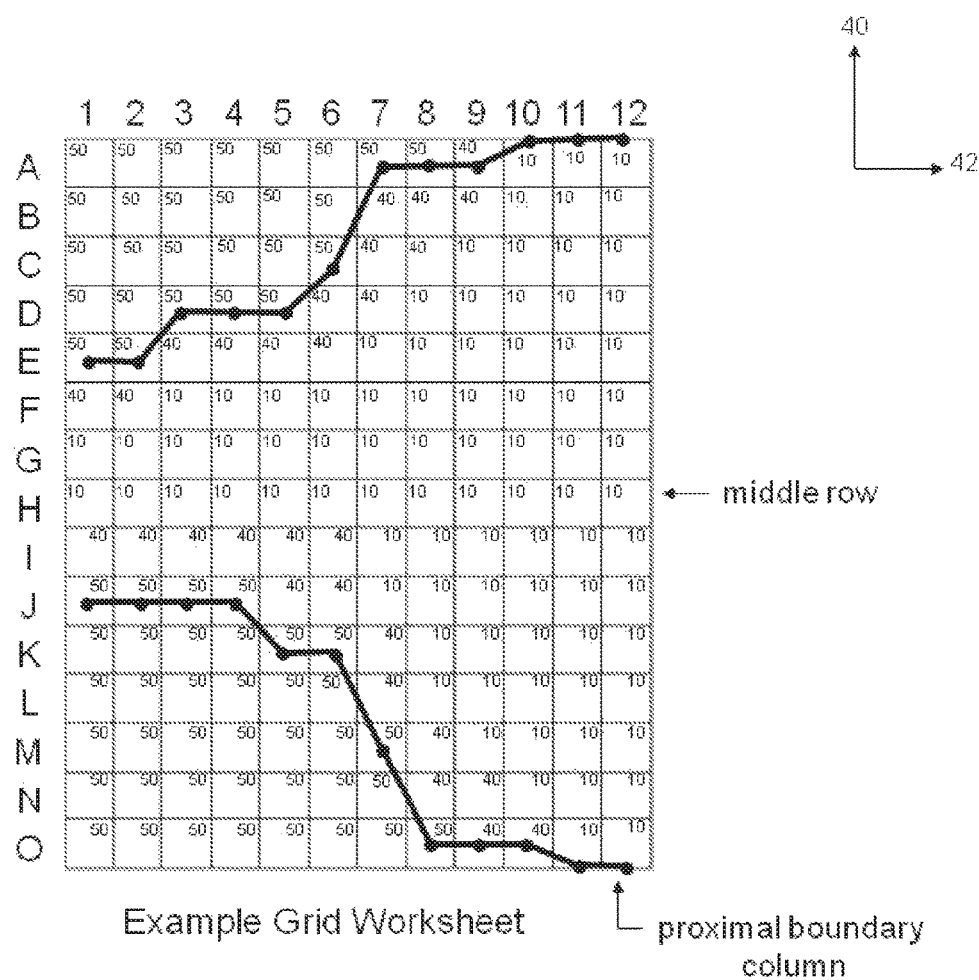
FIG. 12b is a grid worksheet used in the force focused test method.

Mapping of % Extension Regions
1. Identify the row of the grid which is aligned horizontally with the longitudinal center of the fastener. Label this row as the middle row of the grid. (note: this row is not necessarily equidistant between the top and bottom of the grid.)
2. Identify the upper border for the high % extension regions in each column, starting with the far left (distal) column and progressing left to right across the grid.
   a. Choose a column.
   b. Starting at the middle row and progressing up the column to the top of the grid, identify the cells where the % extension is 10% different than the cell directly below it. Choose the boarder cell closest to the top of the grid and mark a boarder point in the center of the cell.
   c. If no boarder cell is found, mark a boarder point at the top vertical edge of the grid, centered horizontally in the cell.
   d. Repeat steps 2a and 2b for each column of interest.
   e. Mark the upper boarder by connecting each of the boarder points to the boarder point in its adjacent column with a line.
3. Identify the lower boarder for the high extension regions in each column, starting with the most distal column and ending with the proximal boundary column.
   a. Choose a column.
   b. Starting at the middle row and progressing down the column to the bottom of the grid, identify the cells where the % extension is 10% different than the cell directly below it. Choose the boarder cell closest to the bottom of the grid and mark a boarder point in the center of the cell.

c. If no boarder cell is found, mark a boarder point at the bottom vertical edge of the grid, centered horizontally in the cell.
d. Repeat steps 3a and 3b for each column of interest.
e. Mark the lower boarder by connecting each of the boarder points to the boarder point in its adjacent column with a line.
4. An example of a completed worksheet is shown in FIG. 12b.

Calculations

Figure 12C:
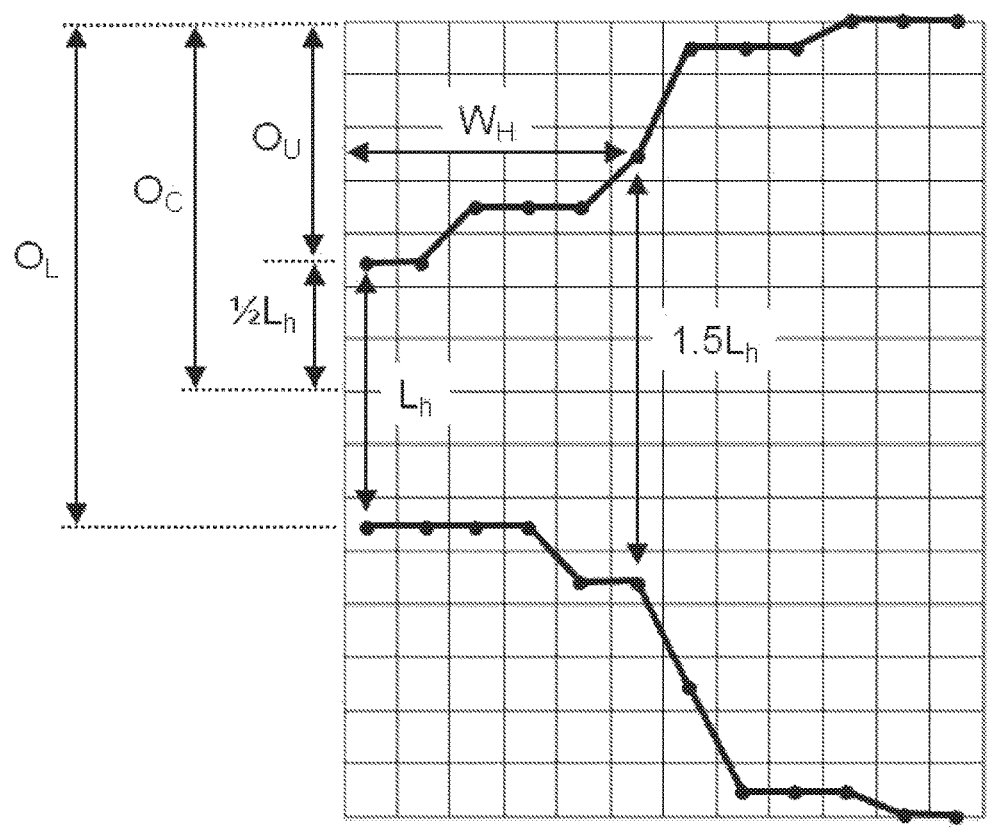
FIG. 12c is a grid worksheet used in the force focused test method.
Figure 13A:
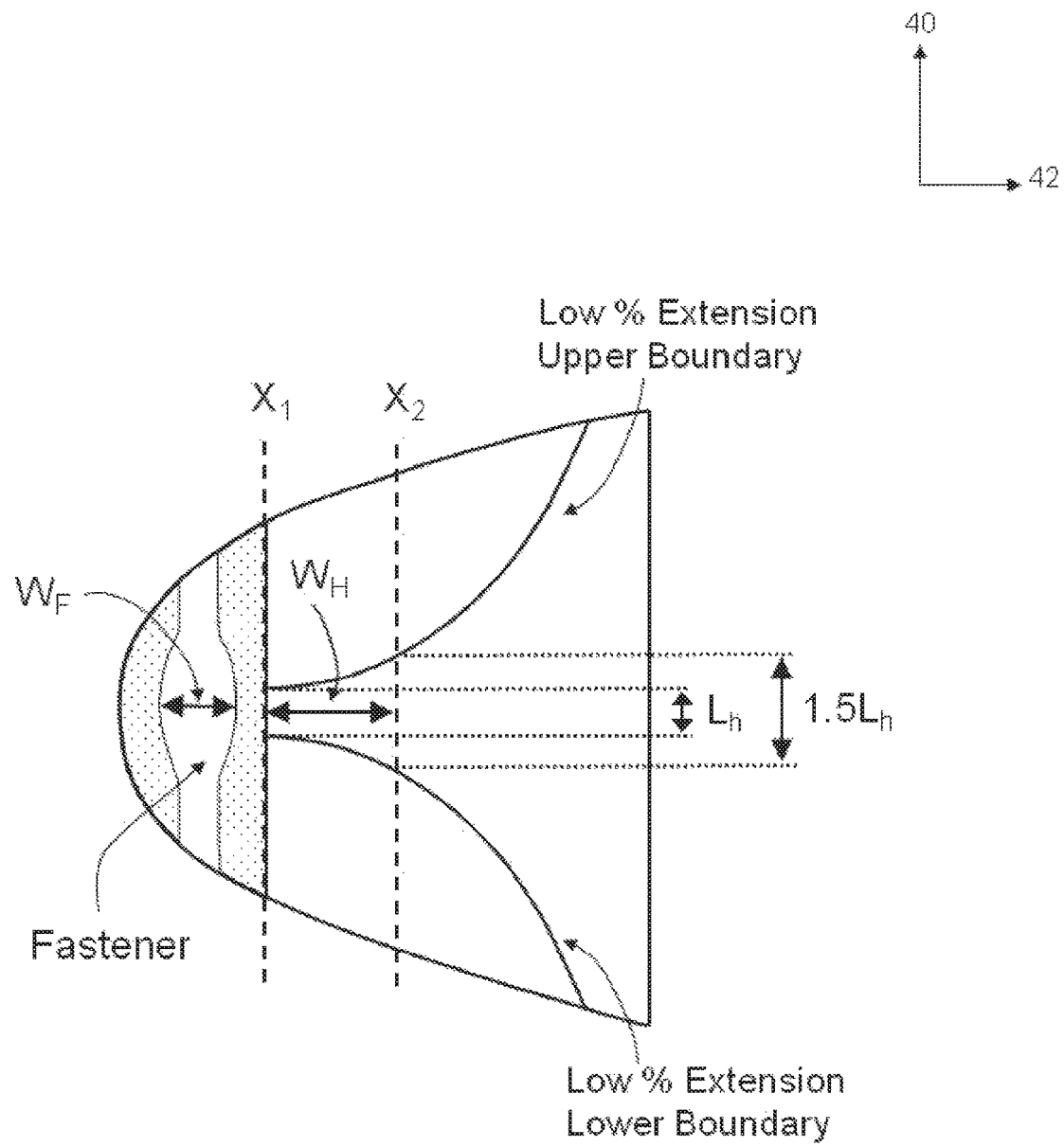
FIG. 13a is a force focused fastening member referenced in the test method.
Figure 13B:
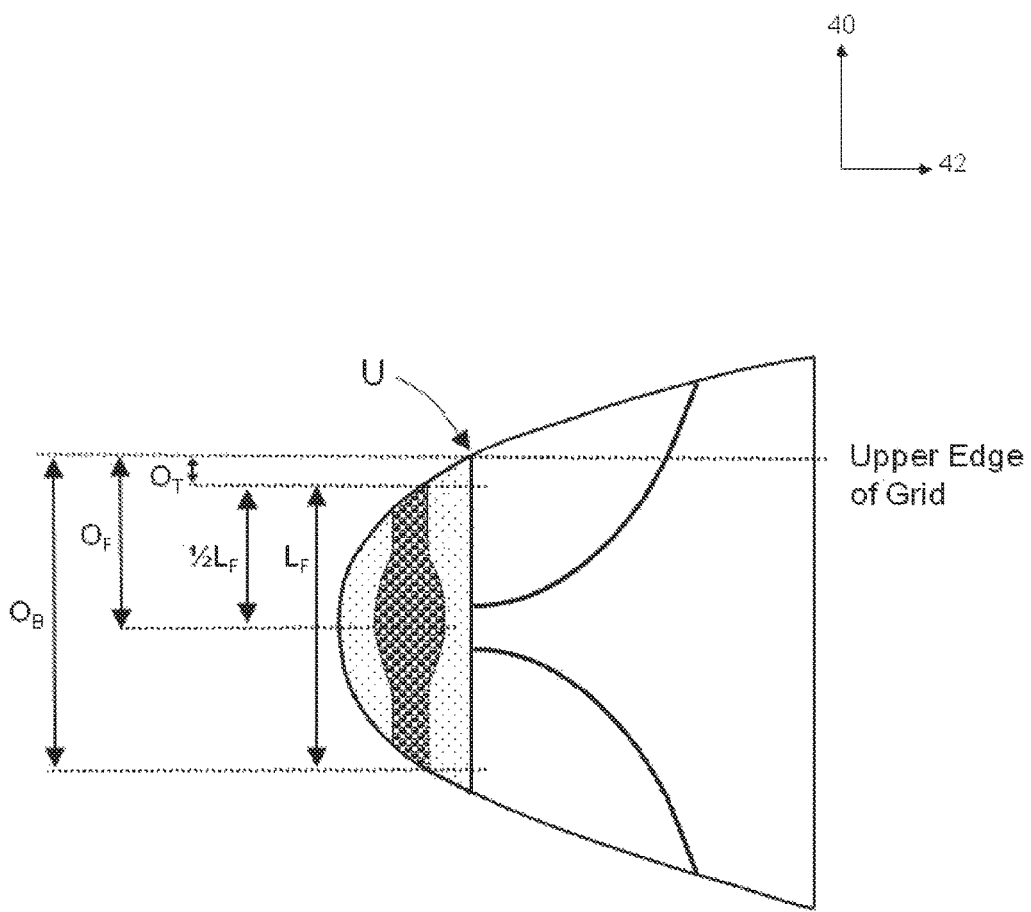
FIG. 13b is a force focused fastening member referenced in the test method.

1. Calculate the relative length of high modulus region adjacent the end region:
   a. Measure the fastener length ($L_F$ in FIG. 13b) as the maximum linear length parallel to the longitudinal axis along the inboard edge of the fastening element.
   b. Using the grid worksheet, calculate the length of the low % extension region ($L_h$ in FIG. 12c) from the most distal column of the worksheet grid. (note: each cell represents 5 mm, each half cell is 2.5 mm).
   c. Calculate the relative length:

Relative length of high modulus region and fastener=$100*L_h/L_F$

2. Calculate the length of offset between longitudinal center line of the high modulus region and the longitudinal center line of the fastening element:
   a. Measure the fastener length ($L_F$ in FIG. 13b) as the maximum linear length parallel to the longitudinal axis along the inboard edge of the fastening element.
   b. Divide the fastening element length ($L_F$ in FIG. 13b) in half. Measure and mark the longitudinal center of fastening element (distance $½L_F$ in FIG. 13b).
   c. Measure from the upper edge of the grid to the longitudinal center of fastening element (distance $O_F$ in FIG. 13b).
   d. Using the grid worksheet, calculate the offset from the top of the grid to the center of the high modulus region (distance $O_c$ in FIG. 12c).
   e. Calculate the relative location as:

Relative location=$100*|O_F-O_C|/L_F$

3. Calculate the length from end portion to high modulus region:
   a. Measure the fastener length ($L_F$ in FIG. 13b) as the maximum linear length parallel to the longitudinal axis along the inboard edge of the fastening element.
   b. Divide the fastening element length ($L_F$ in FIG. 13b) in half. Measure and mark the longitudinal center of fastening element (distance $½L_F$ in FIG. 13b).
   c. Measure from the upper edge of the grid to the longitudinal center of fastening element (distance $O_F$ in FIG. 13b).
   d. Calculate the distance from the upper edge of the grid to the uppermost inboard edge of the fastening element (distance $O_T$ in FIG. 13b) as $O_T=O_F-½L_F$.
   e. Calculate the distance from the upper edge of the grid to the lowermost inboard edge of the fastening element (distance $O_B$ in FIG. 13b) as $O_B=O_F+½L_F$.
   f. Using the grid worksheet, calculate the offset from the top of the grid to the upper boundary of the high modulus region (distance $O_U$ in FIG. 12c).
   g. Again, using the grid worksheet, calculate the offset from the top of the grid to the lower boundary of the high modulus region (distance $O_L$ in FIG. 12c).
   h. Calculate the length from end portion to high modulus region:

$L_1=O_U-O_T$ and $L_2=O_B-O_F$

4. Calculate the relative lateral width of low % extension region:
   a. Measure the fastener width ($W_F$ in FIG. 13a) as the maximum linear length parallel to the lateral width of the fastener.
   b. Determine the lateral width of the low % extension region ($W_H$ in FIG. 13a):
      1. Using the grid worksheet, calculate the longitudinal distance between the upper and lower boundaries of the low % extension region in the far left column ($L_h$ in FIG. 12c).
      2. Move to the next adjacent column to the right.
         If this is the proximal boundary column, calculate $W_H$ as the distance between the upper boarder point in this column and the right edge of the grid.
         Else calculate the distance between the upper and lower boundary. If this distance is 50% greater than $L_h$, calculate $W_H$ as the distance between the upper boarder point in this column and the right edge of the grid.
         Otherwise repeat this step.
   c. Calculate the relative lateral width as:

Relative lateral width=$100*W_H/W_F$

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A force focused fastening member comprising:
an extensible region having a proximal edge, a distal edge transversely opposite the proximal edge and a pair of connecting edges joining the proximal edge to the distal edge, the extensible region having at least a modulus wherein the modulus in a least a portion of the extensible region adjacent the distal edge varies longitudinally and comprises a first high modulus region and a second high modulus region, wherein each of the first and the second high modulus regions comprise a converging end and a diverging end, wherein the diverging end is opposite the converging end;

an end region extending transversely from the distal edge of the extensible region; and a fastener element disposed on the end region, the fastener element having a center portion;

wherein the converging ends of the first and second high modulus regions converge on the center portion and wherein the diverging end of the first high modulus region diverges toward one of the pair of connecting edges and the diverging end of the second high modulus area diverges toward the other of the connecting edges.

2. The force focused fastening member of claim 1 wherein the first and/or the second high modulus regions comprise a longitudinal length, $L_h$, and wherein said longitudinal length, $L_h$, varies transversely.

3. The force focused fastening member of claim 2 wherein the longitudinal length, $L_h$, increases between the distal edge and the proximal edge.

4. The force focused fastening member of claim 1 wherein the extensibility of at least one of the first and second high modulus regions is at least 10% lower than the extensibility of at least one other area in the extensible region.

5. The force focused fastening member of claim 1 wherein the modulus of the first and the second high modulus regions is the same.

6. The force focused fastening member of claim 1 wherein the modulus of the first and the second high modulus regions is different.

7. The force focused fastening member of claim 1 wherein the first high modulus region is at least partially connected to the second high modulus region.

8. The force focused fastening member of claim 1 wherein the first high modulus region and/or the second high modulus region extends from the distal end to the proximal end.

9. The force focused fastening member of claim 1 further comprising a third high modulus region disposed between the first and the second high modulus regions.

10. The force focused fastening member of claim 9 wherein the third high modulus region extends from the distal end to the proximal end.

11. A disposable absorbent article to be worn about the lower torso of a wearer, the disposable absorbent article having a pair of opposing longitudinal side edges, opposing end edges, a first waist region, a second waist region, and a crotch region interposed between the first waist region and the second waist region, the disposable absorbent article comprising:

a topsheet;
a backsheet;
an absorbent core disposed between the topsheet and the backsheet; and
first and second force focused fastening members, each force focused fastening member comprising:

an extensible region having a proximal edge, a distal edge transversely opposite the proximal edge and a pair of connecting edges joining the proximal edge to the distal edge, the extensible region having at least a modulus wherein the modulus in a least a portion of the extensible region adjacent the distal edge varies longitudinally and comprises a first high modulus region and a second high modulus region, each high modulus region comprising a converging end and a diverging end, wherein the diverging end is opposite the converging end;

an end region extending transversely from the distal edge of the extensible region; and a fastener element disposed on the end region, the fastener element having a center portion;

wherein the converging ends of the first and second high modulus regions converge on the center portion and wherein the diverging end of the first high modulus region diverges toward one of the pair of connecting edges and the diverging end of the second high modulus area diverges toward the other of the connecting edges.

12. The disposable absorbent article of claim 11 wherein the first and/or the second high modulus regions comprise a longitudinal length, $L_h$, and wherein said longitudinal length, $L_h$, varies transversely.

13. The disposable absorbent article of claim 12 wherein the longitudinal length, $L_h$, increases between the distal edge and the proximal edge.

14. The disposable absorbent article of claim 11 wherein the extensibility of at least one of the first and second high modulus regions is at least 10% lower than the extensibility of at least one other area in the extensible region.

15. The disposable absorbent article of claim 11 wherein the modulus of the first and the second high modulus regions is the same.

16. The disposable absorbent article of claim 11 wherein the modulus of the first and the second high modulus regions is different.

17. The disposable absorbent article of claim 11 wherein the first high modulus region is at least partially connected to the second high modulus region.

18. The disposable absorbent article of claim 11 wherein the first high modulus region and/or the second high modulus region extends from the distal end to the proximal end.

19. The disposable absorbent article of claim 11 further comprising a third high modulus region disposed between the first and the second high modulus regions.

20. The disposable absorbent article of claim 19 wherein the third high modulus region extends from the distal end to the proximal end.

* * * * *